(12) United States Patent
Zhang et al.

(10) Patent No.: US 12,178,792 B2
(45) Date of Patent: Dec. 31, 2024

(54) PHARMACEUTICAL COMPOSITION AND USE THEREOF IN PREPARING DRUG FOR TREATING TUMOR MULTI-DRUG RESISTANCE

(71) Applicant: SICHUAN JIUZHANG BIOLOGICAL SCIENCE AND TECHNOLOGY CO., LTD., Sichuan (CN)

(72) Inventors: Jie Zhang, Sichuan (CN); Xiaoguang Chen, Sichuan (CN); Huarong Yang, Sichuan (CN); Wang Huang, Sichuan (CN)

(73) Assignee: SICHUAN JIUZHANG BIOLOGICAL SCIENCE AND TECHNOLOGY CO., LTD., Sichuan (CN)

( * ) Notice: Subject to any disclaimer, the term of this patent is extended or adjusted under 35 U.S.C. 154(b) by 1144 days.

(21) Appl. No.: 16/980,576

(22) PCT Filed: Mar. 12, 2019

(86) PCT No.: PCT/CN2019/077826
§ 371 (c)(1),
(2) Date: Dec. 1, 2020

(87) PCT Pub. No.: WO2019/174571
PCT Pub. Date: Sep. 19, 2019

(65) Prior Publication Data
US 2021/0085630 A1     Mar. 25, 2021

(30) Foreign Application Priority Data
Mar. 13, 2018 (CN) .......................... 201810206147.4

(51) Int. Cl.
*A61K 31/216* (2006.01)
*A61P 35/00* (2006.01)

(52) U.S. Cl.
CPC ............ *A61K 31/216* (2013.01); *A61P 35/00* (2018.01)

(58) Field of Classification Search
None
See application file for complete search history.

(56) References Cited

U.S. PATENT DOCUMENTS

| | | | |
|---|---|---|---|
| 10,265,289 B2 * | 4/2019 | Zhang | A61K 31/704 |
| 10,960,042 B2 * | 3/2021 | Lavaud | A61P 29/00 |
| 2003/0229140 A1 * | 12/2003 | Bandyopadhyay | A61K 31/366 514/533 |

FOREIGN PATENT DOCUMENTS

| | | |
|---|---|---|
| CN | 1646112 A | 7/2005 |
| CN | 104758277 A | 7/2015 |
| CN | 106890169 A | 6/2017 |
| CN | 108159038 A | 6/2018 |
| CN | 108498497 A | 9/2018 |

* cited by examiner

*Primary Examiner* — Amanda L. Aguirre
(74) *Attorney, Agent, or Firm* — NKL LAW; Allen Xue

(57) ABSTRACT

A pharmaceutical composition includes chlorogenic acid and coumaroylquinic acid. It can be used for preparing a reversing agent for tumor multi-drug resistance and a PD-1/PD-L1 inhibitor. The combined use of chlorogenic acid and coumaroylquinic acid exhibits a synergistic effect, effectuating a good reversing effect on the drug resistance of a tumor cell strain that produces multi-drug resistance for chemotherapeutic drugs and immunotherapeutic drugs, which may effectively inhibit PD-1/PD-L1 expression in drug-resistant B16 melanoma and drug-resistant Lewis lung cancer mice transplantation tumor tissue, and may effectively proliferate CD4+T and CD8+T cells in drug-resistant B16 melanoma mice and Lewis lung cancer mice.

11 Claims, 7 Drawing Sheets

PHARMACEUTICAL COMPOSITION AND USE THEREOF IN PREPARING DRUG FOR TREATING TUMOR MULTI-DRUG RESISTANCE

TECHNICAL FIELD

The present invention belongs to the field of biomedicine, and in particular to a pharmaceutical composition and its use in the preparation of drugs for treatment of tumor multidrug resistance.

BACKGROUND

Cancer is a major public health problem needed to be resolved in China and even in all parts of the world. On average, millions of people are diagnosed with cancer every year, including more than 200 types of cancer. At present, cancer is one of the main diseases causing death. However, due to the poor selectivity of anti-cancer drugs, single drug treatment has the defects of high toxicity or poor treatment effect, so the research on new generation of low toxicity and high-efficiency drugs has become the top priority of malignant tumor treatment.

The chemical name of dacarbazine is 5-(3,3-dimethyl-1-triazenyl)-4-carboxamideimidazolium citrate. Decarbazine can decompose in vivo and release methyl cation $(CH3)^+$, which plays an alkylation role; meanwhile, it can become a substance similar to the intermediate product of purine biosynthesis, and thus may interfere with purine biosynthesis.

Gemcitabine is a new cytosine nucleoside derivative. Like cytarabine, it is activated by deoxycytidine kinase and metabolized by cytidine deaminase. Gemcitabine is a pyrimidine anticancer drug with the same mechanism as cytarabine. Its main metabolite is incorporated into DNA in cells, and mainly acts on G1/S phase. In clinical practice, gemcitabine is effective for a variety of solid tumors.

OPDIVO® is a human programmed death receptor-1 (PD-1) that is suitable for blocking antibody therapy in following patients: (1) patients with unresectable and metastatic melanoma and ipilimumab, and if BRAF V600 mutation is positive, after administration of BRAF inhibitor, patients with disease progression. (2) After platinum-based chemotherapy, patients with advanced squamous non-small cell lung cancer.

Although dacarbazine, gemcitabine and OPDIVO® can be used to treat cancer, with the increase of medication time, drug resistance will also appear. Once drug resistance occurs, the role of drugs will obviously decline. Nowadays, drug resistance has become a major problem in the medical community. Therefore, it is urgent to develop new drugs to effectively reverse drug resistance.

Content of the Invention

In order to solve above problems, the present invention provides a pharmaceutical composition and its use in the preparation of a drug for treatment of tumor multidrug resistance.

The present invention provides a pharmaceutical composition, that contains chlorogenic acid and coumaroylquinic acid.

Further, the mass ratio of chlorogenic acid to coumaroylquinic acid is 100:0.01~0.5.

Preferably, the mass ratio of chlorogenic acid to coumaroylquinic acid is 100:0.01~0.1.

More preferably, the mass ratio of chlorogenic acid to coumaroylquinic acid is 100:0.05.

The present invention provides a method for preparing the pharmaceutical composition, in which chlorogenic acid and coumaroylquinic acid are used as active components, with the addition of pharmaceutically acceptable excipients, and so a commonly used pharmaceutical preparation is prepared.

Preferably, the preparation is an oral or injectable preparation.

The present invention provides the use of the pharmaceutical composition in the preparation of reversal agent of tumor multidrug resistance.

Wherein, said tumor is melanoma, lung cancer, liver cancer, kidney cancer, glioma, prostate cancer, gastric cancer, bladder cancer, colon cancer, breast cancer, ovarian cancer or cervical cancer.

Preferably, said tumor is melanoma or lung cancer.

Wherein, said pharmaceutical composition is used in combination with the antitumor drug, to prepare a reversal agent of tumor multidrug resistance.

Preferably, said antitumor drug is a chemotherapeutic drug or an immunotherapeutic drug.

More preferably, said chemotherapeutic drug is an imidazole or pyrimidine antitumor drug, preferably dacarbazine or gemcitabine.

Said immunotherapeutic drug is a PD-1 inhibitor, preferably OPDIVO®.

The present invention provides the use of the pharmaceutical composition in the preparation of PD-1/PD-L1 inhibitor.

Wherein, said PD-1/PD-L1 inhibitor is an anti-tumor drug.

Preferably, said anti-tumor drug is a drug against drug-resistant tumor.

More preferably, said drug against drug-resistant tumor is an anti-tumor immunosuppressant.

Further more preferably, said anti-tumor immunosuppressant is a PD-1 inhibitor except for the pharmaceutical composition of the present invention.

Further, except for the pharmaceutical composition of the present invention, said PD-1 inhibitor is OPDIVO®.

The present invention provides a drug combination, that comprises a pharmaceutical composition and an anti-tumor drug administered separately, as well as a pharmaceutically acceptable carrier; said pharmaceutical composition is the one containing chlorogenic acid and coumaroylquinic acid.

Wherein, said antitumor drug is a chemotherapeutic drug or an immunotherapeutic drug.

Preferably, said chemotherapeutic drug is an imidazole or pyrimidine antitumor drug, preferably dacarbazine or gemcitabine.

Said immunotherapeutic drug is a PD-1 inhibitor, preferably OPDIVO®.

Wherein, said tumor is melanoma, lung cancer, liver cancer, kidney cancer, glioma, prostate cancer, gastric cancer, bladder cancer, colon cancer, breast cancer, ovarian cancer or cervical cancer.

Preferably, said tumor is melanoma or lung cancer.

Wherein, the mass ratio of said pharmaceutical composition and the antitumor drug is 1:1.

The mass ratio of chlorogenic acid to coumaroylquinic acid is 100:0.01~0.5.

Preferably, the mass ratio of chlorogenic acid to coumaroylquinic acid is 100:0.01~0.1.

More preferably, the mass ratio of chlorogenic acid to coumaroylquinic acid is 100:0.05.

The present invention provides a pharmaceutical composition comprising chlorogenic acid and coumaroylquinic acid, which can be used to prepare reversal agents of tumor multidrug resistance and PD-1/PD-L1 inhibitors. The experimental results of the present invention indicate that the combined use of chlorogenic acid and coumaroylquinic acid can play a synergistic effect. In particular, the combined use of chlorogenic acid and coumaroylquinic acid has a good reversal effect on tumor cell lines with multi-drug resistance to chemotherapeutic drugs and immunotherapeutic drugs, and can effectively solve the drug resistance of melanoma cell line B16 caused by dacarbazine or Lewis lung cancer induced by gemcitabine, and can effectively inhibit the expression of PD-1/PD-L1 in the transplanted tumor tissues of B16 melanoma and Lewis lung cancer in mice, and can effectively reverse the drug resistance of B16 melanoma cell lines and Lewis lung cancer cell lines caused by OPDIVO®, as well as can effectively act on the proliferation of CD4+T and CD8+T cells in B16 melanoma mice and Lewis lung cancer mice having drug-resistance.

The pharmaceutical composition of the present invention can be used to prepare PD-1/PD-L1 inhibitors, and both of them can play a synergistic effect to reverse the drug resistance.

Obviously, based on above content of the present invention, according to the common technical knowledge and the conventional means in the field, without department from above basic technical spirits, other various modifications, alternations or changes can further be made.

By following specific examples of said embodiments, above content of the present invention is further illustrated. But it should not be construed that the scope of above subject of the present invention is limited to following examples. The techniques realized based on above content of the present invention are all within the scope of the present invention.

EXAMPLES

Figure 1:
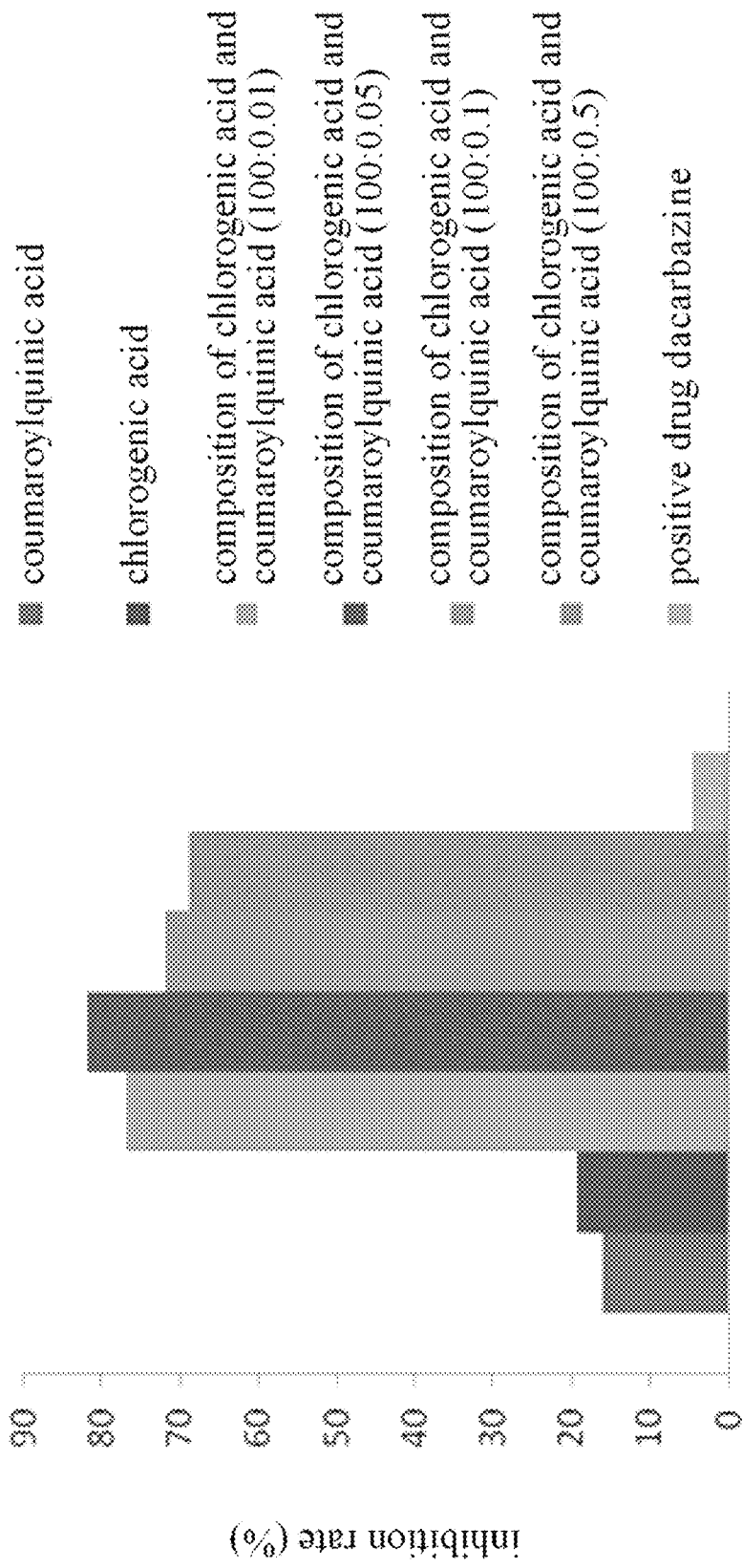
FIG. 1 shows the effects of each experimental group on the weight and the inhibition rate of transplanted-tumor in mice with dacarbazine-resistant B16 melanoma.

The raw materials and equipment used in the specific embodiment of the present invention are all known products, which can be obtained by purchasing those commercially available.

Example 1 the Formula for Oral Preparation of the Pharmaceutical Composition According to the Present Invention 1. Formula 1
1000 g chlorogenic acid, 1 g coumaroylquinic acid.
Preparative method: chlorogenic acid and coumaroylquinic acid were aseptically weighed according to the formula, thoroughly mixed, and aseptically dispensed as pulvis.
2. Formula 2
1000 g chlorogenic acid, 1 g coumaroylquinic acid, 500 g bulking agent, and 5 g binding agent.
Preparative method: chlorogenic acid, coumaroylquinic acid, bulking agent, and binding agent were aseptically weighed according to the formula, granulated, broke, and packaged as granules.
3. Formula 3
1000 g chlorogenic acid, 1 g coumaroylquinic acid, 500 g bulking agent, 5 g binding agent, and 3 g lubricant.
Preparative method: chlorogenic acid, coumaroylquinic acid, bulking agent, and binding agent were weighed according to the formula, granulated, and broke, then lubricant was added. The mixture was pressed to provide tablets.

Above-mentioned bulking agent is one or more of mannitol, lactose, starch, microcrystalline cellulose and dextrin; the binding agent is sodium carboxymethyl cellulose, PVP; the lubricant is magnesium stearate, talc, micronized silica gel.

Example 2 Injection Formula of the Pharmaceutical Composition According to the Present Invention 1. Formula 1
1000 g chlorogenic acid, 1 g coumaroylquinic acid.
Preparative method (1): chlorogenic acid and coumaroylquinic acid were aseptically weighed according to the formula, thoroughly mixed, and aseptically packaged as powder injection.
Preparative method (2): chlorogenic acid and coumaroylquinic acid were weighed according to the formula, dissolved in injectable water, filtered and sterilized, then freeze-dried to obtain freeze-dried powder injection.
2. Formula 2
1000 g chlorogenic acid, 1 g coumaroylquinic acid, 2667 g scaffolding agent, 67 g antioxidant. Preparative method: chlorogenic acid, coumaroylquinic acid, scaffolding agent, and antioxidant were weighed according to the formula, dissolved in injectable water, filtered and sterilized, then freeze-dried to obtain freeze-dried powder injection.

The above-mentioned scaffolding agent are mannitol, lactose, and glucose; the antioxidants are sodium bisulfite, vitamin C, glutathione, and folic acid.

The following examples are used to elucidate the beneficial effects of the present invention.

Experimental Example 1 the Pharmaceutical Composition of the Present Invention and its Separated Constituent Reverse the Drug Resistance of Human Melanoma to the Chemical Drug Dacarbazine In Vitro 1. Materials
1.1 Test drugs
Test drug 1: chlorogenic acid
Test drug 2: coumaroylquinic acid
Test drug 3: composition of chlorogenic acid and coumaroylquinic acid (100:0.01)

Test drug 4: composition of chlorogenic acid and coumaroylquinic acid (100:0.05)
Test drug 5: composition of chlorogenic acid and coumaroylquinic acid (100:0.1)
Test drug 6: composition of chlorogenic acid and coumaroylquinic acid (100:0.5)
Positive drug: dacarbazine (5-(3,3-dimethyl-1-triazenyl)-4-carboxamideimidazolium citrate).

1.2 Cell Lines

A375 melanoma cell lines are those routinely cultured in the laboratory. Cell lines are passaged before use, and the cells that are in a good growth state and grow in the logarithmic phase are selected for use.

2. Experimental Method 2.1 Cultivation of Drug-Resistant Cell Lines

A375 melanoma cell lines were exposed to dacarbazine (400 μg/ml) for 3 months, and centrifuged, to culture dacarbazine-resistant A375 cells. The cells were observed every day, and taken through 3 passages for about 3 days, to ensure cell viability.

2.2 Determining the $IC_{50}$ Values of Dacarbazine Against Cell Lines and Drug-Resistant Strains, and Calculating the Drug-Resistant Index Above-mentioned cell lines and drug-resistant cell lines in the logarithmic growth phase were selected, the cell concentration was adjusted to $8 \times 10^3$ cells/well, and then cells were seeded in a 96-well plate. For the experiment, there were three groups: blank group, control group and dacarbazine group. In the blank group, only medium was added, without inoculating cells; in the control group, medium was added, and cells were inoculated; in the dacarbazine group, medium was added, cells were inoculated, and then dacarbazine was added at different concentrations. The plates were placed in an incubator and incubated for 48 h, then 5 mg/ml MTT (20 μl) was added to each well, and the plate was further incubated for 4 h. The upper liquid was removed, and 150 μl DMSO was added to each well, then the plate was allowed to stand for 30 min until the crystals are completely dissolved. the OD value of each well was measured at 570 nm with a microplate reader to calculate the inhibition rate of tumor cell growth.

The inhibition rate=(1−*OD* value(dacarbazine group−blank group)/*OD* value(control group−blank group))×100%.

Drug-resistant index=$IC_{50}$ value of drug-resistant cells/$IC_{50}$ value of sensitive cells 2.3 Determining the Concentration of Non-Cytotoxic Composition and its Single Compound by MTT Method The culture and treatment methods of cells and drug-resistant cells were the same as above. For the experiment, there were eight groups: blank group, control group and test-drug groups. In the blank group, only medium was added, without inoculating cells; in the control group, medium was added, and cells were inoculated; in the test-drug groups, except for medium and cells, work solutions of test drugs were added at different concentrations, to make a final concentration of 1, 2, 4, 8, 16, 32, 64, and 128 μg/mL. The plates were placed in an incubator and incubated for 48 h, then 5 mg/ml MTT (20 μl) was added to each well, and the plate was further incubated for 4 h. The upper liquid was removed, and 150 μl DMSO was added to each well, then the plate was allowed to stand for 30 min until the crystals are completely dissolved. the OD value of each well was measured at 570 nm with a microplate reader to calculate the inhibition rate of tumor cell growth.

The inhibition rate=(1−*OD* value(test-drug group−blank group)/*OD* value(control group−blank group))×100%, The concentration of each test drug with an inhibition rate of below 10% was regarded as the reversal concentration of the non-toxic dose.

2.4 the Effect of Chlorogenic Acid on Reversing Drug-Resistant Cell Lines

The culture and experimental methods of cells were the same as above.

In the experiment, there are following groups: drug-resistant cell negative group, drug-resistant cells+test drug group 1 (30 μg/ml), drug-resistant cells+test drug group 2 (30 μg/ml), drug-resistant cells+test drug group 3 (30 μg/ml), drug-resistant cells+test drug group 4 (30 μg/ml), drug-resistant cells+test drug group 5 (30 μg/ml), drug-resistant cells+test drug group 6 (30 μg/ml).

Each test drug group was added with different concentrations of dacarbazine, each concentration including 3 replicate wells, and the OD value of each well was measured, to observe whether the cytotoxicity was shown. Each test drug and dacarbazine were respectively used to act on drug resistant cells, so as to compare with the effects of dacarbazine administrated alone on drug-resistant cells, and the $IC_{50}$ value of dacarbazine against drug-resistant cell lines was calculated, as well as the $IC_{50}$ value of each test drug after reversing drug-resistant cell lines.

Reversal index=$IC_{50}$ value before reversal/$IC_{50}$ value after reversal.

2.5 Experimental Results 2.5.1 the Drug-Resistant Index of Dacarbazine and the Non-Cytotoxic Concentration of Each Test Drug for Drug-Resistant A375 Melanoma Cell Lines

TABLE 1

The drug-resistant index of dacarbazine and the non-cytotoxic concentration of each test drug for drug-resistant A375 melanoma cell lines

| Experimental groups | $IC_{50}$ Concentration | $IC_{50}$ Drug-resistant index | Non-cytotoxic concentration (all inhibition rates <10%) |
|---|---|---|---|
| Dacarbazine | 560 μg/ml | 6.22 | — |
| Chlorogenic acid | — | — | 830 μg/ml |
| Coumaroylquinic acid | — | — | 862 μg/ml |
| Composition of chlorogenic acid and coumaroylquinic acid (100:0.01) | — | — | 816 μg/ml |

TABLE 1-continued

The drug-resistant index of dacarbazine and the non-cytotoxic concentration of each test drug for drug-resistant A375 melanoma cell lines

| Experimental groups | IC$_{50}$ | | Non-cytotoxic concentration (all inhibition rates <10%) |
|---|---|---|---|
| | Concentraion | Drug-resistant index | |
| Composition of chlorogenic acid and coumaroylquinic acid (100:0.05) | — | — | 854 µg/ml |
| Composition of chlorogenic acid and coumaroylquinic acid (100:0.1) | — | — | 840 µg/ml |
| Composition of chlorogenic acid and coumaroylquinic acid (100:0.5) | — | — | 852 µg/ml |

Note:
"—" denotes no statistics.

According to above table, the IC$_{50}$ value of dacarbazine against the drug-resistant A375 melanoma cell lines was 560 µg/ml, and the drug-resistant index calculated according to the formula was 6.22; for each test drug, the concentration without significant cytotoxicity (all inhibition rates <10%) was about less than 800 µg/ml.

2.5.2 Reversal Effect of Each Test Drug on Drug-Resistant A375 Melanoma Cell Lines.

TABLE 2

Reversal effect of each test drug on drug-resistant A375 melanoma cell lines.

| Each experimental group | Chlorogenic acid | Coumaroylquinic acid | Composition of chlorogenic acid and coumaroylquinic acid | | | |
|---|---|---|---|---|---|---|
| | | | (100:0.01) | (100:0.05) | (100:0.1) | (100:0.5) |
| IC$_{50}$ of dacarbazine after reversal | 480 µg/ml | 530 µg/ml | 160 µg/ml | 120 µg/ml | 180 µg/ml | 260 µg/ml |
| Reversal index | 1.17 | 1.06 | 3.50 | 4.67 | 3.11 | 2.15 |

After the non-cytotoxic concentration (30 µg/ml) of each test drug group acted on the drug-resistant A375 melanoma cell lines, the IC$_{50}$ value of dacarbazine against the drug-resistant A375 cell lines was very different. Among them, the test drug groups of both chlorogenic acid and coumaroylquinic acid administrated alone had no significant reversal effect on the drug-resistant A375 cell lines, while the test drug groups of the combination of chlorogenic acid and coumaroylquinic acid showed significant reversal effects on drug-resistant A375 cell lines. Both of them had a synergistic effect, and when the ratio of two drugs was 100:0.01~100:0.5, a synergistic effect was observed. With the increase of the proportion of coumaroylquinic acid in the composition, the reversal effect of the composition on the drug-resistant A375 cell lines presented a trend of first increase and then decrease, and thus the best ratio was 100:0.01~100:0.1.

Example 2 the Pharmaceutical Composition of the Present Invention and its Separated Constituent Reverse the Drug Resistance of Human Lung Cancer Cells to the Chemical Drug Gemcitabine In Vitro 1. Materials
1.1 Test Drugs
    Test drug 1: chlorogenic acid
    Test drug 2: coumaroylquinic acid
    Test drug 3: composition of chlorogenic acid and coumaroylquinic acid (100:0.01)
    Test drug 4: composition of chlorogenic acid and coumaroylquinic acid (100:0.05)
    Test drug 5: composition of chlorogenic acid and coumaroylquinic acid (100:0.1)
    Test drug 6: composition of chlorogenic acid and coumaroylquinic acid (100:0.5)
    Positive drug: gemcitabine.
1.2 Cell Lines
    A549 lung cancer cell lines are those routinely cultured in the laboratory. Cell lines are passaged before use, and the cells that are in a good growth state and grow in the logarithmic phase are selected for use.
2. Experimental Method
2.1 Cultivation of Drug-Resistant Cell Lines
    A549 lung cancer cell lines were exposed to gemcitabine (2000 µg/ml) for 3 months, and centrifuged, to culture gemcitabine-resistant A549 cells. The cells were observed every day, and taken through 3 passages for about 3 days, to ensure cell viability.

2.2 Determining the IC$_{50}$ Values of Gemcitabine Against Cell Lines and Drug-Resistant Strains, and Calculating the Drug-Resistant Index Above-mentioned cell lines and drug-resistant cell lines in the logarithmic growth phase were selected, the cell concentration was adjusted to 8×10$^3$ cells/well, and then cells were seeded in a 96-well plate. For the experiment, there were three groups: blank group, control group and gemcitabine group. In the blank group, only medium was added, without inoculating cells; in the control group, medium was added, and cells were inoculated; in the gemcitabine group, medium was added, cells were inoculated, and then gemcitabine was added at different concentrations. The plates were placed in an incubator and incubated for 48 h, then 5 mg/ml MTT (20 µl) was added to each well, and the plate was further incubated for 4 h. The upper liquid was removed, and 150 µl DMSO was added to each well, then the plate was allowed to stand for 30 min until the crystals are completely dissolved. the OD value of each well was measured at 570 nm with a microplate reader to calculate the inhibition rate of tumor cell growth. The inhibition rate=(1−OD value (gemcitabine group−blank group)/OD value (control group−blank group))×100%. Drug-resistant index=$IC_{50}$ value of drug-resistant cells/$IC_{50}$ value of sensitive cells 2.3 Determining the Concentration of Non-Cytotoxic Composition and its Single Compound by MTT Method The culture and treatment methods of cells and drug-resistant cells were the same as above. For the experiment, there were eight groups: blank group, control group and test-drug groups. In the blank group, only medium was added, without inoculating cells; in the control group, medium was added, and cells were inoculated; in the test-drug groups, except for medium and cells, work solutions of test drugs were added at different concentrations, to make a final concentration of 10, 20, 40, 80, 160, 320, 640, and 1280 μg/mL. The plates were placed in an incubator and incubated for 48 h, then 5 mg/ml MTT (20 μl) was added to each well, and the plate was further incubated for 4 h. The upper liquid was removed, and 150 μl DMSO was added to each well, then the plate was allowed to stand for 30 min until the crystals are completely dissolved. the OD value of each well was measured at 570 nm with a microplate reader to calculate the inhibition rate of tumor cell growth. The inhibition rate=(1-OD value (test drug group-blank group)/OD value (control group-blank group))×100%. The concentration of each test drug with an inhibition rate of below 10% was regarded as the reversal concentration of the non-toxic dose.

2.4 the Effect of Chlorogenic Acid on Reversing Drug-Resistant Cell Lines

The culture and experimental methods of cells were the same as above. In the experiment, there are following groups: drug-resistant cell negative group, drug-resistant cells+test drug group 1 (30 μg/ml), drug-resistant cells+test drug group 2 (30 μg/ml), drug-resistant cells+test drug group 3 (30 μg/ml), drug-resistant cells+test drug group 4 (30 μg/ml), drug-resistant cells+test drug group 5 (30 μg/ml), drug-resistant cells+test drug group 6 (30 μg/ml). Each test drug group was respectively added with different concentrations of gemcitabine, each concentration including 3 replicate wells, and the OD value of each well was measured, to observe whether the cytotoxicity was shown. Each test drug and gemcitabine were respectively used to act on drug resistant cells, so as to compare with the effects of gemcitabine administrated alone on drug-resistant cells, and the $IC_{50}$ value of gemcitabine against drug-resistant cell lines was calculated, as well as the $IC_{50}$ value of each test drug after reversing drug-resistant cell lines.

Reversal index=$IC_{50}$ value before reversal/$IC_{50}$ value after reversal.

2.5 Experimental Results 2.5.1 the Drug-Resistant Index of Gemcitabine and the Non-Cytotoxic Concentration of Each Test Drug for Drug-Resistant A549 Lung Cancer Cell Lines

TABLE 3

The drug-resistant index of gemcitabine and the non-cytotoxic concentration of each test drug for drug-resistant A549 lung cancer cell lines

| Experimental groups | $IC_{50}$ Concentration | Drug-resistant index | Non-cytotoxic concentration (all inhibition rates <10%) |
|---|---|---|---|
| Gemcitabine | 3620 μg/ml | 4.63 | — |
| Chlorogenic acid | — | — | 1256 μg/ml |
| Coumaroylquinic acid | — | — | 1142 μg/ml |
| Composition of chlorogenic acid and coumaroylquinic acid (100:0.01) | — | — | 1204 μg/ml |
| Composition of chlorogenic acid and coumaroylquinic acid (100:0.05) | — | — | 1381 μg/ml |
| Composition of chlorogenic acid and coumaroylquinic acid (100:0.1) | — | — | 1017 μg/ml |
| Composition of chlorogenic acid and coumaroylquinic acid (100:0.5) | — | — | 1039 μg/ml |

Note:
"—" denotes no statistics.

According to above table, the $IC_{50}$ value of gemcitabine against the drug-resistant A549 lung cancer cell lines was 3620 μg/ml, and the drug-resistant index calculated according to the formula was 4.63; for each test drug, the concentration without significant cytotoxicity (all inhibition rates <10%) was about less than 1000 g/ml.

2.5.2 Reversal Effect of Each Test Drug on Drug-Resistant A549 Lung Cancer Cell Lines.

TABLE 4

Reversal effect of each test drug on drug-resistant A549 lung cancer cell lines.

| Each experimental group | Chlorogenic acid | Coumaroylquinic acid | Composition of chlorogenic acid and coumaroylquinic acid | | | |
|---|---|---|---|---|---|---|
| | | | (100:0.01) | (100:0.05) | (100:0.1) | (100:0.5) |
| $IC_{50}$ of gemcitabine after reversal | 3203 μg/ml | 3290 μg/ml | 1715 μg/ml | 1477 μg/ml | 1616 μg/ml | 2140 μg/ml |
| Reversal index | 1.13 | 1.10 | 2.11 | 2.45 | 2.24 | 1.69 |

After the non-cytotoxic concentration (30 μg/ml) of each test drug group acted on the drug-resistant A549 lung cancer cell lines, the $IC_{50}$ value of gemcitabine against the drug-resistant A549 cell lines was very different. Among them, the test drug groups of both chlorogenic acid and coumaroylquinic acid administrated alone had no significant reversal effect on the drug-resistant A549 cell lines, while the test drug groups of the combination of chlorogenic acid and coumaroylquinic acid showed significant reversal effects on drug-resistant A549 cell lines; and when the ratio of two drugs was 100:0.01~100:0.5, both of them reached a synergistic effect. With the increase of the proportion of coumaroylquinic acid in the composition, the reversal effect of the composition on the drug-resistant A549 cell lines presented a trend of first increase and then decrease, and thus the best ratio was 100:0.01~100:0.1.

Summary: according to the experimental results of Examples 1 and 2 above, the combination of chlorogenic acid and coumaroylquinic acid has a good effect on reversing drug resistance of tumor cell lines with chemical drug resistance. Chlorogenic acid and coumaroylquinic acid have synergistic effect, and the combination of chlorogenic acid: coumaroylquinic acid with a ratio of 100:0.01~100:0.1 shows the most significant effect.

Example 3 Animal Experiment 1 on the Treatment of Drug Resistance by the Composition and the Single Compound (Chemotherapeutic Drugs)

1 Experimental Materials
1.1 Test Drugs
  Test drug 1: chlorogenic acid
  Test drug 2: coumaroylquinic acid
  Test drug 3: composition of chlorogenic acid and coumaroylquinic acid (100:0.01)
  Test drug 4: composition of chlorogenic acid and coumaroylquinic acid (100:0.05)
  Test drug 5: composition of chlorogenic acid and coumaroylquinic acid (100:0.1)
  Test drug 6: composition of chlorogenic acid and coumaroylquinic acid (100:0.5)
  Positive drug 1: dacarbazine (5-(3,3-dimethyl-1-triazenyl)-4-carboxamideimidazolium citrate).
  Positive drug 2: gemcitabine
1.2 Test Cell Lines
B16 melanoma cell lines were induced by the increased gradient concentration of dacarbazine, and established by clone screening and cultured without drug before the experiment. Lewis lung cancer cell lines were induced by the increased gradient concentration of gemcitabine, and established by clone screening and cultured without drug before the experiment.

1.3 Test Animals
  BABL/C-nu mice, ♀, weighing 18~22 g;
2 Experimental Method
2.1 Establishment of Tumor Model in Experimental Animals
After the drug was removed from the drug-resistant cell lines, the cell concentration was adjusted to $1\times10^7$/ml with the culture medium. $1\times10^7$/ml of cells were subcutaneously injected into the right armpit of mice, 0.1 ml per mouse.
2.2 Administration Method
After the average diameter of tumor reached 100 mm, the mice were randomly divided into test drug group 1, test drug group 2, test drug group 3, test drug group 4, test drug group 5, test drug group 6, positive drug group, and negative group, respectively.

Test drug group: the test drug group was first intraperitoneally injected, once a day, 30 mg/kg/time, for 5 consecutive days; administration was stopped, and the positive drug was given by intraperitoneal injection on the next day; wherein the positive drug dacarbazine was administrated once every other day, 60 mg/kg/time; wherein the positive drug gemcitabine was given once every other day, 300 mg/kg/time.

Positive drug group: positive drug dacarbazine was given once every other day, 60 mg/kg/time; positive drug gemcitabine was given once every other day, 300 mg/kg/time.

Negative group: normal saline was intraperitoneally injected, once a day, for 15 consecutive days.
2.3 Evaluation of Antitumor Effect
After completion of administration, the experiment was stopped, and the mice were killed by cervical dislocation and weighed. The tumor was stripped and weighed, to calculate the tumor inhibition rate.

Tumor inhibition rate %=[1−(the average tumor weight in the drug group/the average tumor weight in the negative group)]×100%.

2.4 Expression of PD-1/PD-L1
The positive expression rate of PD-1/PD-L1 in tumor tissues was detected by immunohistochemical SP method.
2.5 Determination of the Number of CD4+T and CD8+T Lymphocytes
The number of CD4+T and CD8+T lymphocytes was analyzed by immunofluorescence staining, and the average number of CD4+T and CD8+T cells infiltrated in 6 high power fields was counted.
3 Experimental Results
3.1 Effect of Each Experimental Group on the Inhibition Rate of Drug-Resistant Transplanted Tumor

TABLE 5

Effect of each experimental group on the tumor weight and the tumor inhibition rate of mice with dacarbazine-resistant B16 melanoma ($\bar{x} \pm s$)

| Groups | Dose (mg · kg$^{-1}$) | Animal numbers (n) | Tumor weight (g) | Tumor inhibition rate (%) |
|---|---|---|---|---|
| Coumaroylquinic acid | 30 | 8 | 2.22 ± 0.26 | 15.91 |
| Chlorogenic acid | 30 | 8 | 2.13 ± 0.52*Δ | 19.32 |
| Composition of chlorogenic acid and coumaroylquinic acid (100:0.01) | 30 | 8 | 0.61 ± 0.25**ΔΔ | 76.89 |
| Composition of chlorogenic acid and coumaroylquinic acid (100:0.05) | 30 | 8 | 0.48 ± 0.31**ΔΔ | 81.82 |
| Composition of chlorogenic acid and coumaroylquinic acid (100:0.1) | 30 | 8 | 0.74 ± 0.48**ΔΔ | 71.97 |
| Composition of chlorogenic acid and coumaroylquinic acid (100:0.5) | 30 | 8 | 0.82 ± 0.69**ΔΔ | 68.94 |
| Positive drug dacarbazine | 60 | 8 | 2.52 ± 0.77 | 4.55 |
| Negative control group | N.S | 8 | 2.64 ± 0.64 | — |

Compared with the negative group, *p < 0.05, **p < 0.01; compared with the positive drug dacarbazine group, Δp < 0.05, ΔΔp < 0.01.

From Table 5 and FIG. 1, it can be shown that the positive drug group has a lower inhibitory rate on the transplanted tumor of B16 melanoma in mice, and is not observed obvious inhibitory effect on the tumor. However, in the test drug groups, coumaroylquinic acid, chlorogenic acid and the combination of chlorogenic acid and coumaroylquinic acid have good inhibitory effect on drug-resistant B16 melanoma, of which the inhibitory rate of the composition of chlorogenic acid and coumaroylquinic acid is significant, indicating that the combination of chlorogenic acid and coumaroylquinic acid can effectively solve the drug resistance of B16 melanoma cell lines caused by dacarbazine. In addition, according to the separated inhibitory effect of coumaroylquinic acid and chlorogenic acid in the test drug groups, their tumor inhibition rates were far lower than that of the combination of chlorogenic acid and coumaroylquinic acid, indicating that the combination of chlorogenic acid and coumaroylquinic acid can well reverse the drug resistance of B16 melanoma cell lines caused by dacarbazine, and the synergistic effect of chlorogenic acid and coumaroylquinic acid is found.

TABLE 6

Effect of each experimental group on the tumor weight and the tumor inhibition rate of mice with gemcitabine-resistant Lewis lung cancer ($\bar{x} \pm s$)

| Groups | Dose (mg · kg$^{-1}$) | Animal number (n) | Tumor weight (g) | Tumor inhibitory rate (%) |
|---|---|---|---|---|
| Coumaroylquinic acid | 30 | 8 | 2.16 ± 0.41 | 5.68 |
| Chlorogenic acid | 30 | 8 | 2.05 ± 0.79 | 10.48 |
| Composition of chlorogenic acid and coumaroylquinic acid (100:0.01) | 30 | 8 | 0.55 ± 0.22**ΔΔ | 75.98 |
| Composition of chlorogenic acid and coumaroylquinic acid (100:0.05) | 30 | 8 | 0.48 ± 0.31**ΔΔ | 79.04 |
| Composition of chlorogenic acid and coumaroylquinic acid (100:0.1) | 30 | 8 | 0.65 ± 0.52**ΔΔ | 71.62 |
| Composition of chlorogenic acid and coumaroylquinic acid (100:0.5) | 30 | 8 | 0.78 ± 0.63**ΔΔ | 65.94 |
| Positive drug gemcitabine | 300 | 8 | 2.17 ± 0.89 | 5.24 |
| Negative control group | N.S | 8 | 2.29 ± 0.63 | — |

Compared with the negative group, *$p < 0.05$, **$p < 0.01$; compared with the positive drug gemcitabine group, $\Delta p < 0.05$, $\Delta\Delta p < 0.01$.

Figure 2:
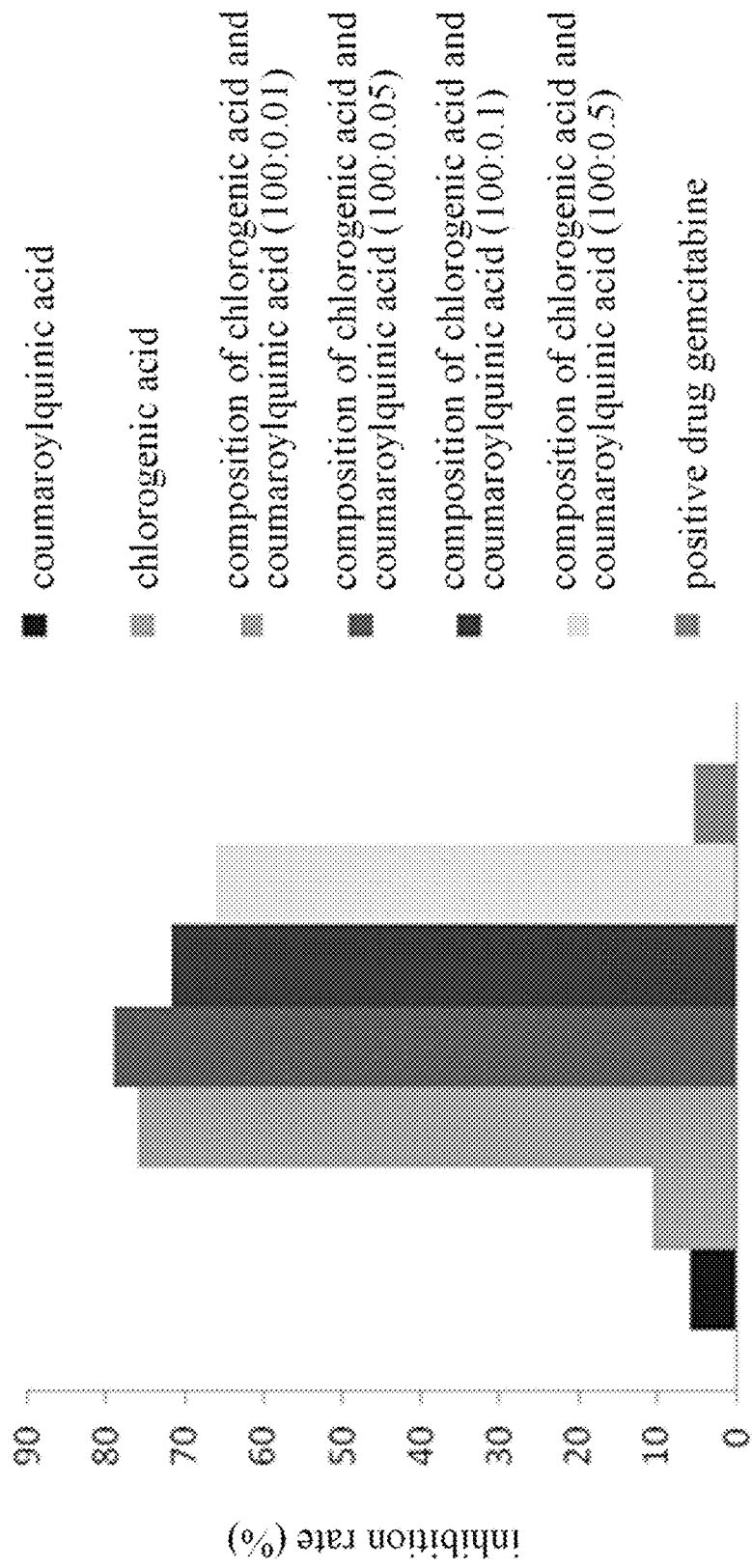
FIG. 2 shows the effects of each experimental group on the weight and the inhibition rate of transplanted-tumor in mice with gemcitabine-resistant Lewis lung cancer.

From Table 6 and FIG. 2, it can be shown that the positive drug group has a lower inhibitory rate on the transplanted tumor of Lewis lung cancer in mice, and is not observed obvious inhibitory effect on the tumor. However, in the test drug groups, coumaroylquinic acid, chlorogenic acid and the combination of chlorogenic acid and coumaroylquinic acid have good inhibitory effect on drug-resistant Lewis lung cancer, of which the inhibitory rate of the composition of chlorogenic acid and coumaroylquinic acid is significant, indicating that the combination of chlorogenic acid and coumaroylquinic acid can effectively solve the drug resistance of Lewis lung cancer caused by gemcitabine. In addition, according to the separated inhibitory effect of coumaroylquinic acid and chlorogenic acid in the test drug groups, their tumor inhibition rates were far lower than that of the combination of chlorogenic acid and coumaroylquinic acid, indicating that the combination of chlorogenic acid and coumaroylquinic acid can well reverse the drug resistance of Lewis lung cancer caused by gemcitabine, and the synergistic effect of chlorogenic acid and coumaroylquinic acid is found. 3.2 Expression of PD-1/PD-L1 in drug-resistant transplanted tumor of each experimental group

TABLE 7

Expression rate of PD-1/PD-L1 in transplanted tumor tissues of drug-resistant B16 melanoma in mice of each experimental group (%)

| Groups | positive PD-L1 |
|---|---|
| Coumaroylquinic acid | 73.39% |
| Chlorogenic acid | 72.26% |
| Composition of chlorogenic acid and coumaroylquinic acid (100:0.01) | 36.34% |
| Composition of chlorogenic acid and coumaroylquinic acid (100:0.05) | 31.58% |
| Composition of chlorogenic acid and coumaroylquinic acid (100:0.1) | 40.71% |
| Composition of chlorogenic acid and coumaroylquinic acid (100:0.5) | 46.08% |
| Positive drug dacarbazine | 72.51% |
| Negative control group | 76.24% |

TABLE 8

Expression rate of PD-1/PD-L1 in transplanted tumor tissues of drug-resistant Lewis lung cancer in mice of each experimental group (%)

| Groups | Positive PD-L1 |
|---|---|
| Coumaroylquinic acid | 79.23% |
| Chlorogenic acid | 81.83% |
| Composition of chlorogenic acid and coumaroylquinic acid (100:0.01) | 34.14% |
| Composition of chlorogenic acid and coumaroylquinic acid (100:0.05) | 32.27% |
| Composition of chlorogenic acid and coumaroylquinic acid (100:0.1) | 39.28% |
| Composition of chlorogenic acid and coumaroylquinic acid (100:0.5) | 43.66% |
| Positive drug gemcitabine | 78.93% |
| Negative control group | 83.06% |

The results showed that the combination of chlorogenic acid and coumaroylquinic acid could effectively inhibit the expression of PD-1/PD-L1 in the transplanted tumor tissues of drug-resistant B16 melanoma and Lewis lung cancer in mice, and both of them had synergistic effect. Among them, the composition of chlorogenic acid: coumarinic acid in the ratio of 100:0.01~100:0.05 was the best.

3.3 the Number of CD4+T and CD8+ T Cells in Drug-Resistant Transplanted Tumor of Each Experimental Group

TABLE 9

The number of CD4 + T and CD8 + T cells in transplanted tumor of drug-resistant B16 melanoma in mice of each experimental group (x ± s)

| Groups | CD4 + T cells | CD8 + T cells |
| --- | --- | --- |
| Coumaroylquinic acid | 62.83 ± 7.51 | 91.53 ± 3.54 |
| Chlorogenic acid | 69.43 ± 4.72 | 88.62 ± 5.38 |
| Composition of chlorogenic acid and coumaroylquinic acid (100:0.01) | 90.26 ± 2.27** ΔΔ | 186.68 ± 2.99** ΔΔ |
| Composition of chlorogenic acid and coumaroylquinic acid (100:0.05) | 93.74 ± 1.85** ΔΔ | 192.41 ± 5.61** ΔΔ |
| Composition of chlorogenic acid and coumaroylquinic acid (100:0.1) | 86.81 ± 6.38** ΔΔ | 170.45 ± 1.25** ΔΔ |
| Composition of chlorogenic acid and coumaroylquinic acid (100:0.5) | 83.42 ± 3.64** ΔΔ | 165.47 ± 3.44** ΔΔ |
| Positive drug dacarbazine | 63.67 ± 5.83 | 91.23 ± 3.84 |
| Negative control group | 58.48 ± 3.64 | 86.56 ± 2.06 |

Compared with the negative group, $*p < 0.05$, $**p < 0.01$; compared with the positive drug dacarbazine, $\Delta p < 0.05$, $\Delta\Delta p < 0.01$.

TABLE 10

The number of CD4 + T and CD8 + T lymphocytes in transplanted tumor of drug-resistant Lewis lung cancer in mice of each experimental group (x ± s)

| Groups | CD4 + T cells | CD8 + T cells |
| --- | --- | --- |
| Coumaroylquinic acid | 78.75 ± 6.39 | 98.53 ± 4.98 |
| Chlorogenic acid | 80.63 ± 5.08 | 106.62 ± 6.88 |
| Composition of chlorogenic acid and coumaroylquinic acid (100:0.01) | 125.42 ± 5.23** ΔΔ | 215.67 ± 7.36** ΔΔ |
| Composition of chlorogenic acid and coumaroylquinic acid (100:0.05) | 131.14 ± 7.38** ΔΔ | 232.12 ± 10.21** ΔΔ |
| Composition of chlorogenic acid and coumaroylquinic acid (100:0.1) | 118.65 ± 4.02** ΔΔ | 196.34 ± 7.05** ΔΔ |
| Composition of chlorogenic acid and coumaroylquinic acid (100:0.5) | 102.35 ± 5.26** ΔΔ | 188.36 ± 2.63** ΔΔ |
| Positive drug gemcitabine | 82.16 ± 1.42 | 112.53 ± 4.28 |
| Negative control group | 76.28 ± 2.66 | 103.42 ± 5.24 |

Compared with the negative group, $*p < 0.05$, $**p < 0.01$; compared with the positive drug gemcitabine, $\Delta p < 0.05$, $\Delta\Delta p < 0.01$.

The results showed that by comparing the experimental group of the combination of chlorogenic acid and coumaroylquinic acid with the positive drug group (dacarbazine and gemcitabine), the number of CD4+T and CD8+ T cells was significantly increased, indicating that the combination of chlorogenic acid and coumaroylquinic acid can effectively promote the proliferation of CD4+T and CD8+ T cells in mice with drug-resistant B16 melanoma and Lewis lung cancer, and chlorogenic acid and coumaroylquinic acid have synergistic effect.

Example 4 Animal Experiment 2 on the Treatment of Drug Resistance by the Composition and the Single Compound (Immunotherapeutic Drugs)

1 Experimental Materials
1.1 Test Drugs
  Test drug 1: composition of chlorogenic acid and coumaroylquinic acid (100:0.01)
  Test drug 2: composition of chlorogenic acid and coumaroylquinic acid (100:0.05)
  Test drug 3: composition of chlorogenic acid and coumaroylquinic acid (100:0.1)
  Test drug 4: composition of chlorogenic acid and coumaroylquinic acid (100:0.5)
  Positive drug: OPDIVO®
  Single drug 1: g chlorogenic acid
  Single drug 2: coumaroylquinic acid
1.2 Test Cell Lines
  B16 melanoma cell lines; Lewis lung cancer cell lines.
1.3 Test Animals
  BABL/C-nu mice, ♀, weighing 18~22 g;
2 Experimental Method
2.1 Establishment of OPDIVO®-Resistant Tumor Model in Experimental Animals The concentration of cell lines was adjusted to $1\times10^7$/ml with the culture medium. $1\times10^7$/ml of cells were subcutaneously injected into the right armpit of mice, 0.1 ml per mouse. On the second day after inoculation, the model group was intraperitoneally injected with OPDIVO®, 30 mg/kg, once every other day; in the blank group, the same amount of saline was intraperitoneally injected on the second day after inoculation, once every other day; the tumor volume was measured before each administration, and the administration of model group was stopped after the tumor volume exponentially increased and there was no significant difference from the tumor volume of blank group.

2.2 Administration Method

The model mice were randomly divided into groups, eight for one group, and included test drug group 1, test drug group 2, test drug group 3, test drug group 4, positive drug OPDIVO® group, single drug chlorogenic acid group, test drug 1+OPDIVO® group, test drug 2+OPDIVO® group, test drug 3+OPDIVO® group, test drug 4+OPDIVO® group, and negative group, respectively.

Test drug group: from the second day after stopping administration to the model, the group received drug by intraperitoneal injection, once a day, 30 mg/kg.

Single drug group: from the second day after stopping administration to the model, the group received drug by intraperitoneal injection, once a day, 30 mg/kg.

Test drug+OPDIVO® group: from the second day after stopping administration to the model, the group received the test drug by intraperitoneal injection, once a day, and the test drug was stopped after administrating for 5 consecutive days; on the next day, OPDIVO® was intraperitoneally injected, once every other day, with the dosage of 30 mg/kg.

Positive drug group: once every other day, 30 mg/kg.

Negative group: normal saline was intraperitoneally injected, once a day, the same amount of saline.

Before each administration, the tumor volume was measured, and the experiment was stopped when the average tumor volume of negative group was greater than 1.5 cm³.

2.3 Evaluation of Antitumor Effect

After completion of administration, the experiment was stopped, and the mice were killed by cervical dislocation and weighed. The tumor was stripped and weighed, to calculate the tumor inhibition rate.

Tumor inhibition rate %=[1−(the average tumor weight in the drug group/the average tumor weight in the negative group)]×100%.

2.4 Expression of PD-1/PD-L1

The positive expression rate of PD-1/PD-L1 in tumor tissues was detected by immunohistochemical SP method.

2.5 Determination of the Number of CD4+T and CD8+T Lymphocytes

The number of CD4+T and CD8+T lymphocytes was analyzed by immunofluorescence staining, and the average number of CD4+T and CD8+T cells infiltrated in 6 high power fields was counted.

3 Experimental Results 3.1 Tumor Volume of Drug-Resistant Model Group and Blank Group

TABLE 11

Tumor volume of mice with B16 melanoma cell lines in drug-resistant model group and blank group (x ± s)

| Time after inoculation | Model group (cm³) | Blank group (cm³) |
|---|---|---|
| 2 d | 0.00 ± 0.000 ** | 0.088 ± 0.052 |
| 4 d | 0.084 ± 0.047 ** | 0.179 ± 0.043 |
| 6 d | 0.106 ± 0.043 ** | 0.244 ± 0.039 |
| 8 d | 0.128 ± 0.062 ** | 0.402 ± 0.205 |
| 10 d | 0.179 ± 0.147 ** | 0.605 ± 0.300 |
| 12 d | 0.286 ± 0.116 ** | 0.899 ± 0.795 |
| 14 d | 0.881 ± 0.204 | 1.036 ± 0.532 |

Compared with the blank group, *p < 0.05, ** p < 0.01.

TABLE 12

Tumor volume of mice with Lewis lung cancer cell lines in drug-resistant model group and blank group (x ± s)

| Time after inoculation | Model group (cm³) | Blank group (cm³) |
|---|---|---|
| 4 d | 0.00 ± 0.000 ** | 0.062 ± 0.052 |
| 6 d | 0.073 ± 0.052* | 0.116 ± 0.106 |
| 8 d | 0.098 ± 0.075** | 0.187 ± 0.099 |
| 10 d | 0.121 ± 0.101** | 0.334 ± 0.147 |
| 12 d | 0.164 ± 0.084** | 0.576 ± 0.378 |
| 14 d | 0.226 ± 0.113** | 0.741 ± 0.439 |
| 16 d | 0.464 ± 0.154* | 0.994 ± 0.648 |
| 18 d | 0.984 ± 0.236 | 1.147 ± 0.522 |

Compared with the negative group, *p < 0.05, **p < 0.01

Figure 3:
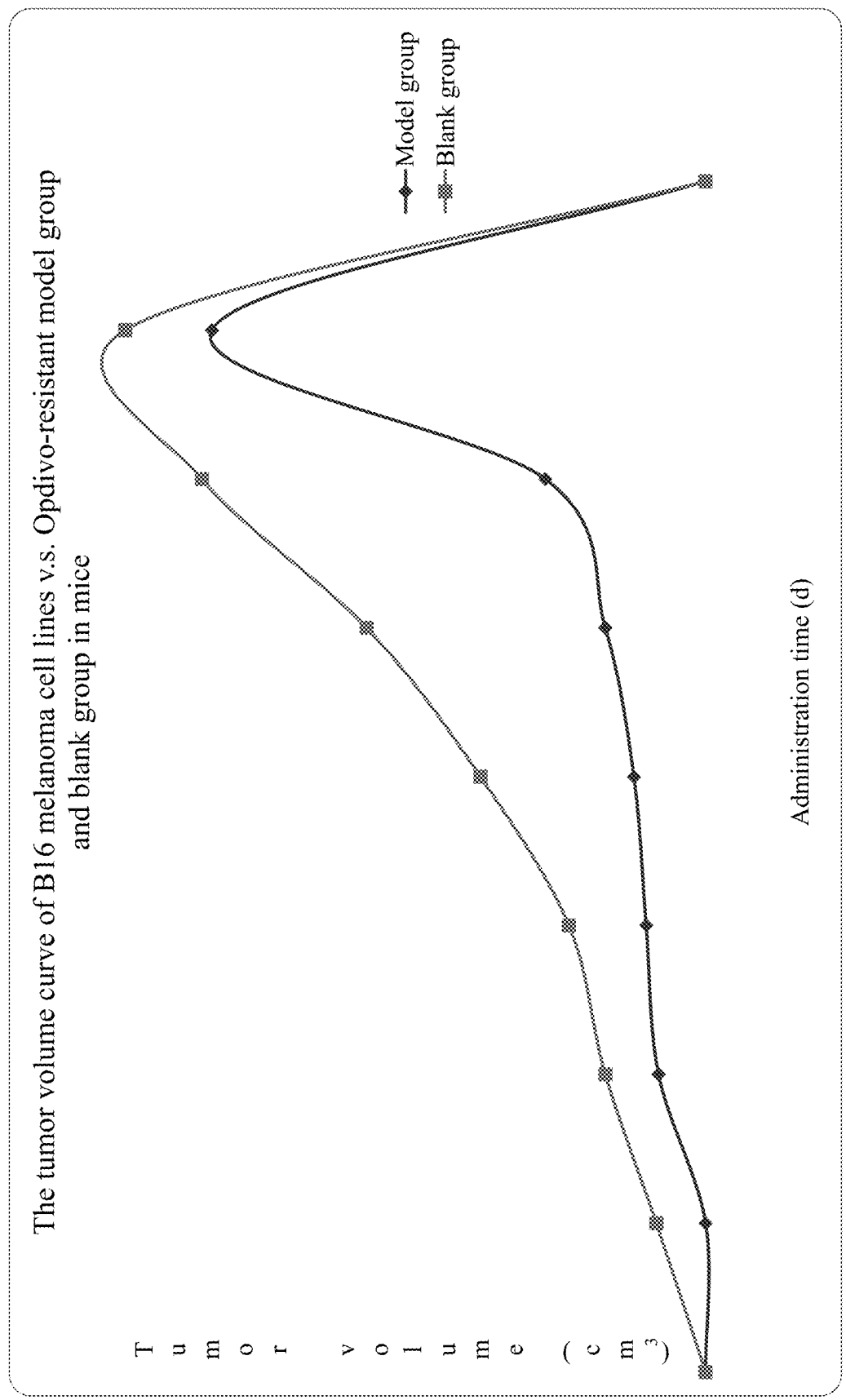
FIG. 3 shows the tumor volume curve of B16 melanoma cell lines v.s. OPDIVO®-resistant model group and blank group in mice.
Figure 4:
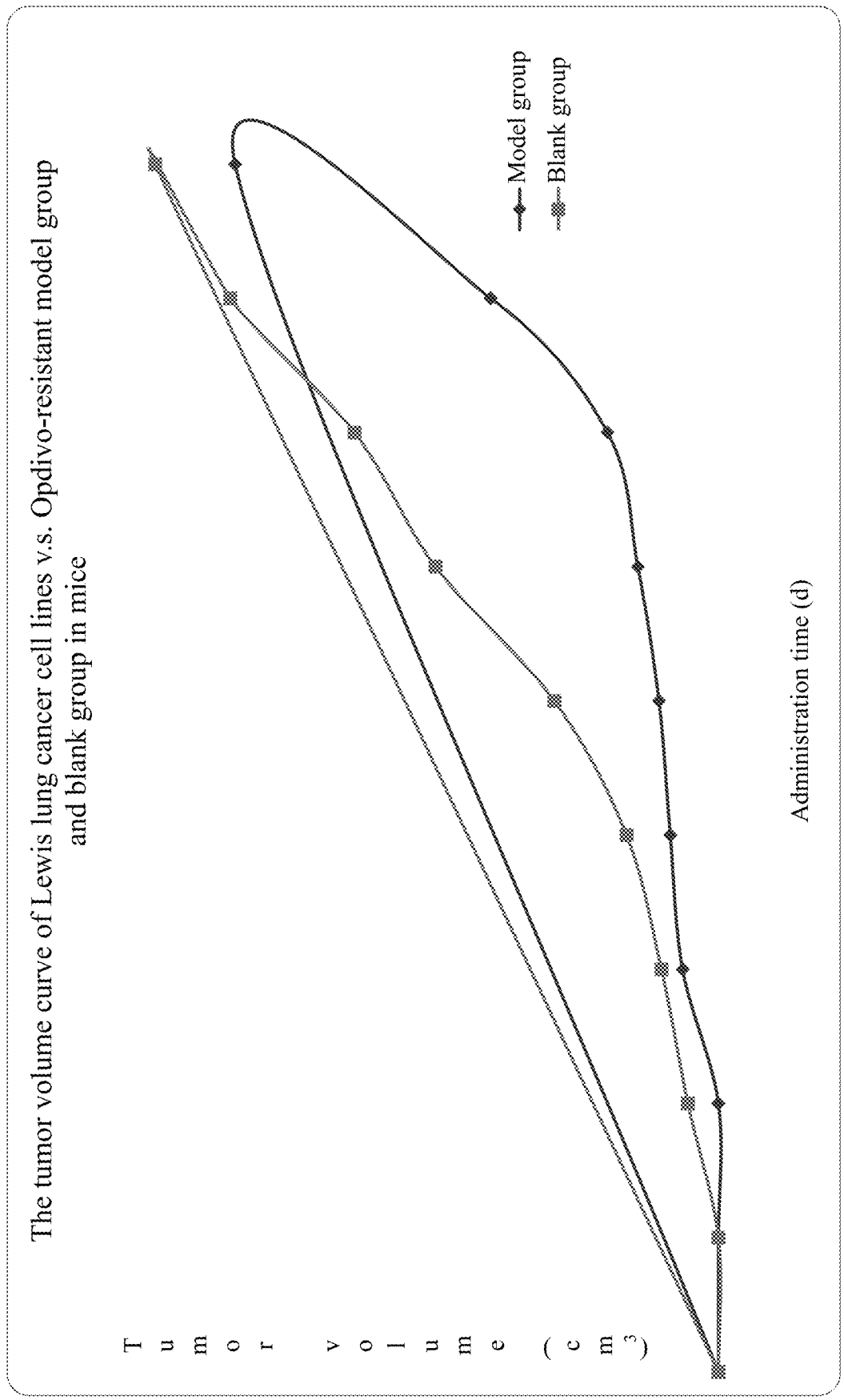
FIG. 4 shows the tumor volume curve of Lewis lung cancer cell lines v.s. OPDIVO®-resistant model group and blank group in mice.

From Tables 11 and 12 as well as FIGS. 3 and 4, it is shown that the tumor volume of the model group of B16 melanoma cell lines was basically equivalent to that of blank group after intraperitoneal injection of OPDIVO® for 14 days, and there was no significant difference; After mice in model group of Lewis lung cancer cell lines were intraperitoneally injected with OPDIVO® for 18 days, the tumor volume was almost the same as that of the blank group, and there was no significant difference between both of groups, indicating that the mice had developed resistance to OPDIVO® in the course of continuous administration.

3.2 Effect of Each Experimental Group on Tumor Volume of Drug-Resistant Model Group

TABLE 13

Effect of each experimental group on tumor volume of mice with B16 melanoma cell lines in drug-resistant model group (x ± s)

| Groups | Dose (mg·kg⁻¹) | Animal numbers (n) | Tumor volume (cm³) |
|---|---|---|---|
| Coumaroylquinic acid | 30 | 7 | 1.762 ± 0.947 |
| Chlorogenic acid | 30 | 7 | 1.788 ± 0.539 |
| Composition of chlorogenic acid:coumaroylquinic acid (100:0.01) | 30 | 8 | 1.552 ± 0.248*Δ |
| Composition of chlorogenic acid:coumaroylquinic acid (100:0.05) | 30 | 8 | 1.546 ± 0.681*Δ |
| Composition of chlorogenic acid:coumaroylquinic acid (100:0.1) | 30 | 8 | 1.591 ± 0.996*Δ |
| Composition of chlorogenic acid:coumaroylquinic acid (100:0.5) | 30 | 7 | 1.608 ± 0.537*Δ |
| Composition of chlorogenic acid:coumaroylquinic acid (100:0.01) + positive drug Opdivo | 30 + 30 | 8 | 1.181 ± 0.204** ΔΔ |
| Composition of chlorogenic acid:coumaroylquinic acid (100:0.05) + positive drug Opdivo | 30 + 30 | 8 | 1.084 ± 0.538** ΔΔ |
| Composition of chlorogenic acid:coumaroylquinic acid (100:0.1) + positive drug Opdivo | 30 + 30 | 8 | 1.245 ± 0.661** ΔΔ |
| Composition of chlorogenic acid:coumaroylquinic acid (100:0.5) + positive drug Opdivo | 30 | 8 | 1.327 ± 0.704**Δ |
| Positive drug Opdivo | 30 | 6 | 1.793 ± 0.842 |
| Negative group | N.S | 5 | 1.828 ± 0.917 |

Compared with the negative group, *p < 0.05, **p < 0.01; compared with the positive drug Opdivo group, Δp < 0.05, ΔΔ p < 0.01.

Experimental results showed that the continuous treatment effect of positive drug OPDIVO® on drug-resistant B16 melanoma cell line mice was not obvious, and the effect of single drug chlorogenic acid on tumor volume control was not obvious; the tumor volume in the combination group of chlorogenic acid and coumaroylquinic acid was different from that of positive drug OPDIVO® group and negative group (P<0.05), indicating that the control effect on tumor volume was obvious. In the experimental group of the combination of chlorogenic acid and coumaroylquinic acid+ OPDIVO®, the effect of continuous treatment on drug-resistant mice is very significant, and compared with the positive drug OPDIVO® group and the negative group, there was an extremely significant difference (P<0.01), indicating that the combination of chlorogenic acid and coumaroylquinic acid could effectively reverse the drug resistance of B16 melanoma mice induced by OPDIVO®, so that OPDIVO® could continue to play an anti-tumor effect.

TABLE 14

Effect of each experimental group on tumor volume of model group of drug-resistant Lewis lung cancer mice (x ± s).

| Groups | Dose (mg·kg⁻¹) | Animal number (n) | Tumor volume (cm³) |
|---|---|---|---|
| Coumaroylquinic acid | 30 | 8 | 1.584 ± 0.424 |
| Chlorogenic acid | 30 | 8 | 1.592 ± 0.704 |

TABLE 14-continued

Effect of each experimental group on tumor volume of model group of drug-resistant Lewis lung cancer mice (x ± s).

| Groups | Dose (mg · kg⁻¹) | Animal number (n) | Tumor volume (cm³) |
|---|---|---|---|
| Composition of chlorogenic acid:coumaroylquinic acid (100:0.01) | 30 | 8 | 1.428 ± 0.356*Δ |
| Composition of chlorogenic acid:coumaroylquinic acid (100:0.05) | 30 | 8 | 1.401 ± 0.412*Δ |
| Composition of chlorogenic acid:coumaroylquinic acid (100:0.1) | 30 | 8 | 1.412 ± 0.458*Δ |
| Composition of chlorogenic acid:coumaroylquinic acid (100:0.5) | 30 | 8 | 1.441 ± 0.307*Δ |
| Composition of chlorogenic acid:coumaroylquinic acid (100:0.01) + positive drug Opdivo | 30 + 30 | 8 | 1.138 ± 0.836**ΔΔ |
| Composition of chlorogenic acid:coumaroylquinic acid (100:0.05) + positive drug Opdivo | 30 + 30 | 8 | 1.016 ± 0.472**ΔΔ |
| Composition of chlorogenic acid:coumaroylquinic acid (100:0.1) + positive drug Opdivo | 30 + 30 | 8 | 1.159 ± 0.865**ΔΔ |
| Composition of chlorogenic acid:coumaroylquinic acid (100:0.5) + positive drug Opdivo | 30 | 8 | 1.183 ± 0.631**ΔΔ |
| Positive drug Opdivo | 30 | 6 | 1.616 ± 0.772 |
| Negative group | N.S | 6 | 1.648 ± 0.851 |

Compared with the negative group, *p < 0.05, **p < 0.01; compared with the positive drug Opdivo group, Δp < 0.05, ΔΔp < 0.01.

Experimental results showed that the continuous treatment effect of positive drug OPDIVO® on drug-resistant Lewis lung cancer mice was not obvious, and the effect of single drug chlorogenic acid on tumor volume control was not obvious; the tumor volume in the combination group of chlorogenic acid and coumaroylquinic acid was different from that of positive drug OPDIVO® group and negative group (P<0.05), indicating that the control effect on tumor volume was obvious. In the experimental group of the combination of chlorogenic acid and coumaroylquinic acid+OPDIVO®, the effect of continuous treatment on drug-resistant mice is very significant, and compared with the positive drug OPDIVO® group and the negative group, there was an extremely significant difference (P<0.01), indicating that the combination of chlorogenic acid and coumaroylquinic acid could effectively reverse the drug resistance of Lewis lung cancer mice induced by OPDIVO®, so that OPDIVO® could continue to play an anti-tumor effect.

3.3 Effect of Each Experimental Group on the Tumor Inhibition Rate of Drug-Resistant Model Group

TABLE 15

Effect of each experimental group on tumor weight and tumor inhibition rate of B16 melanoma mice with drug resistance (x ± s).

| Groups | Dose (mg · kg⁻¹) | Animal number (n) | Tumor weight (g) | Tumor inhition rate (%) |
|---|---|---|---|---|
| Coumaroylquinic acid | 30 | 7 | 2.71 ± 0.46 | 4.24 |
| Chlorogenic acid | 30 | 7 | 2.74 ± 0.59 | 3.18 |
| Composition of chlorogenic acid:coumaroylquinic acid (100:0.01) | 30 | 8 | 2.42 ± 0.86 *Δ | 14.49 |
| Composition of chlorogenic acid:coumaroylquinic acid (100:0.05) | 30 | 8 | 2.41 ± 0.91 *Δ | 14.84 |
| Composition of chlorogenic acid:coumaroylquinic acid (100:0.1) | 30 | 8 | 2.46 ± 0.85 *Δ | 13.07 |
| Composition of chlorogenic acid:coumaroylquinic acid (100:0.5) | 30 | 7 | 2.51 ± 0.97 *Δ | 11.31 |
| Composition of chlorogenic acid:coumaroylquinic acid (100:0.01) + positive drug Opdivo | 30 + 30 | 8 | 1.86 ± 0.69 **ΔΔ | 34.28 |
| Composition of chlorogenic acid:coumaroylquinic acid (100:0.05) + positive drug Opdivo | 30 + 30 | 8 | 1.64 ± 1.02 **ΔΔ | 42.05 |
| Composition of chlorogenic acid:coumaroylquinic acid (100:0.1) + positive drug Opdivo | 30 + 30 | 8 | 1.98 ± 0.99 **ΔΔ | 30.04 |
| Composition of chlorogenic acid:coumaroylquinic acid (100:0.5) + positive drug Opdivo | 30 + 30 | 8 | 2.21 ± 0.38 **ΔΔ | 21.91 |
| Positive drug Opdivo | 30 | 6 | 2.79 ± 1.13 | 1.41 |
| Negative group | N.S | 5 | 2.83 ± 0.82 | — |

Compared with the negative group, * p < 0.05, ** p < 0.01; compared with the positive drug Opdivo group, Δp < 0.05, ΔΔp < 0.01.

Figure 5:
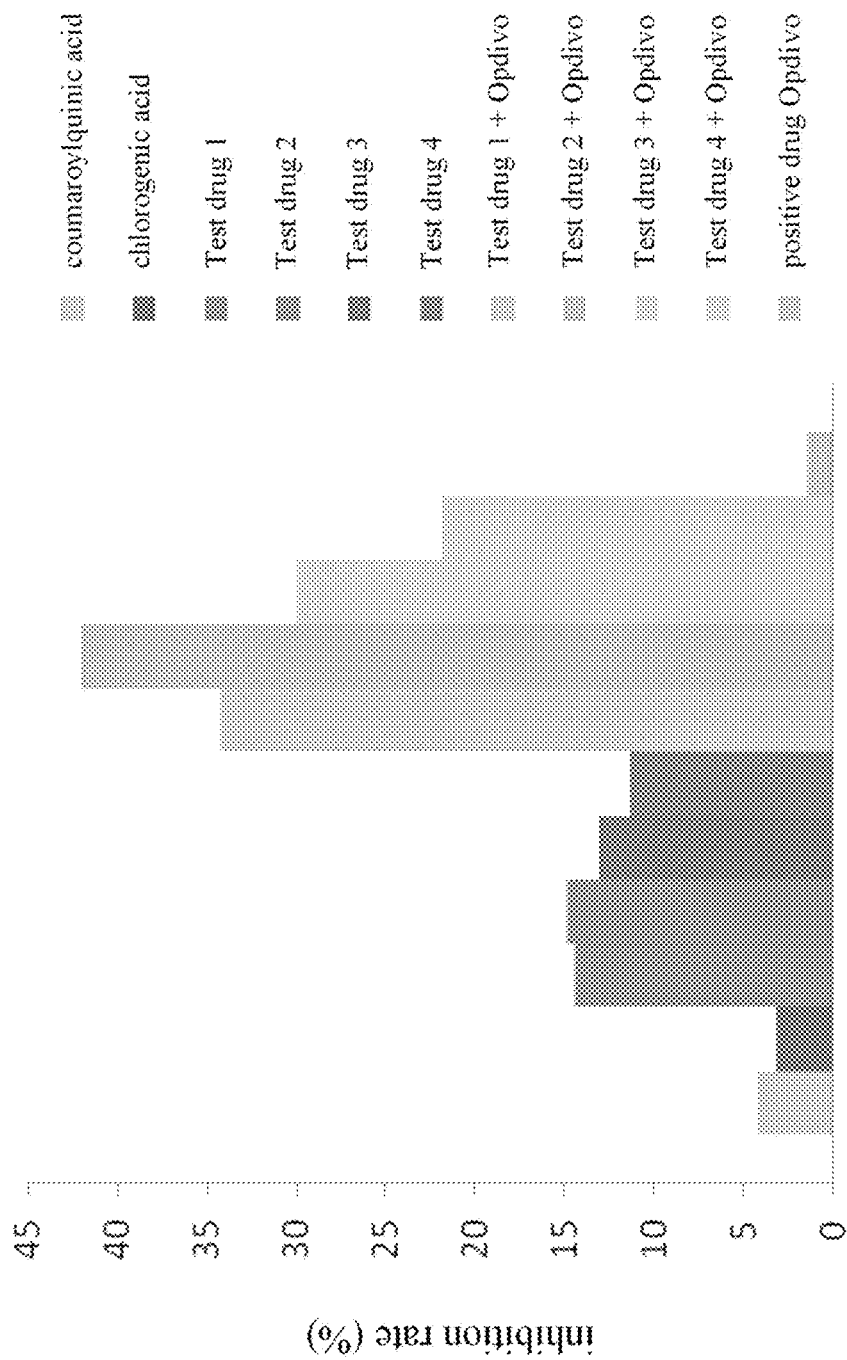
FIG. 5 shows the effect of each experimental group on the tumor inhibition rate of Opivo-resistant B16 melanoma in mice.

From Table 15 and FIG. 5, it was shown that the continuous treatment effect of positive drug OPDIVO® on drug-resistant B16 cancer mice was not obvious, and the tumor inhibition rate of single drug chlorogenic acid was lower; the tumor inhibition rate in the combination group of chlorogenic acid and coumaroylquinic acid was different from that of positive drug OPDIVO® group and negative group (P<0.05). In the experimental group of the combination of chlorogenic acid and coumaroylquinic acid+OPDIVO®, the effect of continuous treatment on drug-resistant mice is very significant, and compared with the positive drug OPDIVO® group and the negative group, there was an extremely significant difference (P<0.01), indicating that the combination of chlorogenic acid and coumaroylquinic acid could well reverse the drug resistance of B16 melanoma mice induced by OPDIVO®.

TABLE 16

Effect of each experimental group on tumor weight and tumor inhibition rate of Lewis lung cancer mice with drug resistance (x ± s).

| Groups | Dose (mg·kg$^{-1}$) | Animal numbers (n) | Tumor weight (g) | Tumor inhibition rate (%) |
|---|---|---|---|---|
| Coumaroylquinic acid | 30 | 8 | 2.48 ± 0.55 | 3.88 |
| Chlorogenic acid | 30 | 8 | 2.46 ± 0.72 | 3.18 |
| Composition of chlorogenic acid:coumaroylquinic acid (100:0.01) | 30 | 8 | 2.26 ± 0.78*Δ | 14.16 |
| Composition of chlorogenic acid:coumaroylquinic acid (100:0.05) | 30 | 8 | 2.22 ± 0.53*Δ | 16.22 |
| Composition of chlorogenic acid:coumaroylquinic acid (100:0.1) | 30 | 8 | 2.28 ± 0.74*Δ | 13.16 |
| Composition of chlorogenic acid:coumaroylquinic acid (100:0.5) | 30 | 8 | 2.25 ± 0.55*Δ | 14.67 |
| Composition of chlorogenic acid:coumaroylquinic acid (100:0.01) + positive drug Opdivo | 30 + 30 | 8 | 1.77 ± 0.79 **ΔΔ | 45.76 |
| Composition of chlorogenic acid:coumaroylquinic acid (100:0.05) + positive drug Opdivo | 30 + 30 | 8 | 1.52 ± 0.83 **ΔΔ | 69.74 |
| Composition of chlorogenic acid:coumaroylquinic acid (100:0.1) + positive drug Opdivo | 30 + 30 | 8 | 1.81 ± 1.28 **ΔΔ | 42.54 |
| Composition of chlorogenic acid:coumaroylquinic acid (100:0.5) + positive drug Opdivo | 30 + 30 | 8 | 1.92 ± 0.95 **ΔΔ | 34.38 |
| Positive drug Opdivo | 30 | 6 | 2.52 ± 0.83 | 2.38 |
| Negative group | N.S | 6 | 2.58 ± 0.71 | — |

Compared with the negative group, *p < 0.05, ** p < 0.01; compared with the positive drug Opdivo group, Δp < 0.05, ΔΔp < 0.01.

Figure 6:
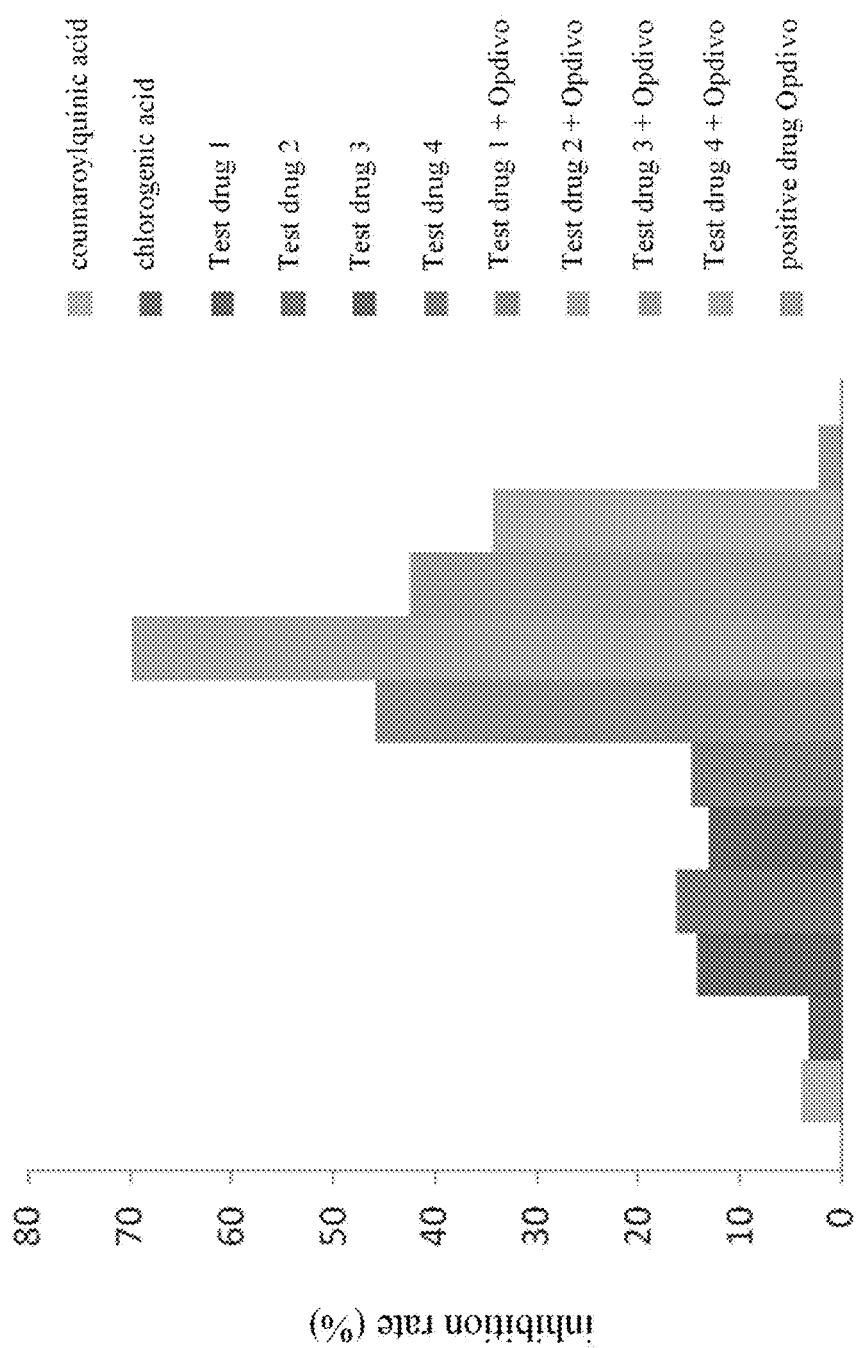
FIG. 6 shows the effect of each experimental group on the tumor inhibition rate of Opivo-resistant Lewis lung cancer in mice.

From Table 16 and FIG. 6, it was shown that the continuous treatment effect of positive drug OPDIVO® on drug-resistant Lewis lung cancer mice was not obvious, and the tumor inhibition rate of single drug chlorogenic acid was lower; the tumor inhibition rate in the combination group of chlorogenic acid and coumaroylquinic acid was different from that of positive drug OPDIVO® group and negative group (P<0.05). In the experimental group of the combination of chlorogenic acid and coumaroylquinic acid+OPDIVO®, the effect of continuous treatment on drug-resistant mice was very significant, and compared with the positive drug OPDIVO® group and the negative group, there was an extremely significant difference (P<0.01), indicating that the combination of chlorogenic acid and coumaroylquinic acid could well reverse the drug resistance of Lewis lung cancer mice induced by OPDIVO®.

3.4 the Expression of PD-1/PD-L1 in Drug-Resistant Tumors of Each Experimental Group

TABLE 17

Expression rate of PD-1/PD-L1 in tumor tissues of drug-resistant B16 melanoma mice in each experimental group (%)

| Groups | Positive PD-L1 |
|---|---|
| Coumaroylquinic acid | 82.87% |
| Chlorogenic acid | 83.41% |
| Composition of chlorogenic acid:coumaroylquinic acid (100:0.01) | 73.28% |
| Composition of chlorogenic acid:coumaroylquinic acid (100:0.05) | 72.83% |
| Composition of chlorogenic acid:coumaroylquinic acid (100:0.1) | 74.27% |
| Composition of chlorogenic acid:coumaroylquinic acid (100:0.5) | 76.99% |
| Composition of chlorogenic acid:coumaroylquinic acid (100:0.01) + positive drug Opdivo | 52.72% |
| Composition of chlorogenic acid:coumaroylquinic acid (100:0.05) + positive drug Opdivo | 46.78% |
| Composition of chlorogenic acid:coumaroylquinic acid (100:0.1) + positive drug Opdivo | 58.14% |
| Composition of chlorogenic acid:coumaroylquinic acid (100:0.5) + positive drug Opdivo | 62.59% |
| Positive drug Opdivo | 85.87% |
| Negative group | 86.32% |

TABLE 18

Expression rate of PD-1/PD-L1 in tumor tissues of drug-resistant Lewis lung cancer mice in each experimental group (%)

| Groups | Positive PD-L1 |
|---|---|
| Coumaroylquinic acid | 71.89% |
| Chlorogenic acid | 70.36% |
| Composition of chlorogenic acid:coumaroylquinic acid (100:0.01) | 64.57% |
| Composition of chlorogenic acid:coumaroylquinic acid (100:0.05) | 63.85% |
| Composition of chlorogenic acid:coumaroylquinic acid (100:0.1) | 65.03% |
| Composition of chlorogenic acid:coumaroylquinic acid (100:0.5) | 65.49% |
| Composition of chlorogenic acid:coumaroylquinic acid (100:0.01) + positive drug Opdivo | 39.07% |
| Composition of chlorogenic acid:coumaroylquinic acid (100:0.05) + positive drug Opdivo | 36.84% |
| Composition of chlorogenic acid:coumaroylquinic acid (100:0.1) + positive drug Opdivo | 42.38% |
| Composition of chlorogenic acid:coumaroylquinic acid (100:0.5) + positive drug Opdivo | 46.92% |
| Positive drug Opdivo | 72.77% |
| Negative group | 72.64% |

Experimental results showed that the expression of PD-1/PD-L1 in tumor tissues of drug-resistant B16 melanoma and Lewis lung cancer mice was not significantly inhibited by positive drug OPDIVO® group and single drug chlorogenic acid group, but inhibited by the combination of chlorogenic acid and coumaroylquinic acid, while the inhibitory effect in the test group of the combination of chlorogenic acid and coumaroylquinic acid+OPDIVO® was significant, indicating that the combination of chlorogenic acid and coumaroylquinic acid can effectively inhibit the expression of PD-1/PD-L1 in the tumor tissues of OPDIVO®-resistant B16 melanoma and Lewis lung cancer mice.

3.5 the Number of CD4+T and CD8+T Cells in Drug-Resistant Transplanted Tumor of Each Experimental Group

TABLE 19

The number of CD4 + T and CD8 + T cells in drug-resistant B16 melanoma mice of each experimental group (x ± s)

| Groups | CD4 + T cells | CD8 + T cells |
|---|---|---|
| Coumaroylquinic acid | 75.09 ± 5.23 | 88.26 ± 5.36 |
| Chlorogenic acid | 74.63 ± 6.35 | 89.42 ± 2.52 |
| Composition of chlorogenic acid:coumaroylquinic acid (100:0.01) | 90.25 ± 4.53*Δ | 132.53 ± 4.738*Δ |
| Composition of chlorogenic acid:coumaroylquinic acid (100:0.05) | 92.07 ± 2.36*Δ | 138.62 ± 4.28*Δ |
| Composition of chlorogenic acid:coumaroylquinic acid (100:0.1) | 88.43 ± 4.64*Δ | 127.36 ± 7.368*Δ |
| Composition of chlorogenic acid:coumaroylquinic acid (100:0.5) | 86.98 ± 3.52*Δ | 122.09 ± 5.388*Δ |
| Composition of chlorogenic acid:coumaroylquinic acid (100:0.01) + positive drug Opdivo | 116.65 ± 3.67** ΔΔ | 200.48 ± 5.08** ΔΔ |
| Composition of chlorogenic acid:coumaroylquinic acid (100:0.05) + positive drug Opdivo | 124.74 ± 6.58** ΔΔ | 214.53 ± 9.97** ΔΔ |
| Composition of chlorogenic acid:coumaroylquinic acid (100:0.1) + positive drug Opdivo | 111.84 ± 10.05** ΔΔ | 194.35 ± 7.85** ΔΔ |
| Composition of chlorogenic acid:coumaroylquinic acid (100:0.5) + positive drug Opdivo | 105.31 ± 7.93** ΔΔ | 186.64 ± 2.86** ΔΔ |
| Positive drug Opdivo | 74.63 ± 6.35 | 88.61 ± 5.82 |
| Negative group | 72.37 ± 3.74 | 86.49 ± 6.35 |

Compared with the negative group, *p < 0.05, **p < 0.01; compared with the positive drug Opdivo group, Δp < 0.05, ΔΔ p < 0.01.

TABLE 20

The number of CD4 + T and CD8 + T lymphocytes in drug-resistant Lewis lung cancer mice of each experimental group (x ± s).

| Groups | CD4 + T cells | CD8 + T cells |
|---|---|---|
| Coumaroylquinic acid | 65.12 ± 5.17 | 113.64 ± 8.23 |
| Chlorogenic acid | 66.52 ± 4.63 | 119.38 ± 6.55 |
| Composition of chlorogenic acid:coumaroylquinic acid (100:0.01) | 85.53 ± 8.77*Δ | 161.33 ± 3.55*Δ |
| Composition of chlorogenic acid:coumaroylquinic acid (100:0.05) | 89.14 ± 10.63*Δ | 177.57 ± 11.71*Δ |
| Composition of chlorogenic acid:coumaroylquinic acid (100:0.1) | 80.21 ± 5.95*Δ | 154 ± 9.52*Δ |
| Composition of chlorogenic acid:coumaroylquinic acid (100:0.5) | 78.53 ± 8.357*Δ | 151 ± 13.05*Δ |
| Composition of chlorogenic acid:coumaroylquinic acid (100:0.01) + positive drug Opdivo | 127.84 ± 9.53** ΔΔ | 247.84 ± 9.03** ΔΔ |
| Composition of chlorogenic acid:coumaroylquinic acid (100:0.05) + positive drug Opdivo | 131.08 ± 4.98** ΔΔ | 254.66 ± 7.72** ΔΔ |
| Composition of chlorogenic acid:coumaroylquinic acid (100:0.1) + positive drug Opdivo | 118.52 ± 9.26** ΔΔ | 224.38 ± 12.96** ΔΔ |
| Composition of chlorogenic acid:coumaroylquinic acid (100:0.5) + positive drug Opdivo | 111.63 ± 4.36** ΔΔ | 204.6 ± 5.63** ΔΔ |
| Positive drug Opdivo | 64.22 ± 7.74 | 117.81 ± 7.99 |
| Negative group | 61.41 ± 6.08 | 115.83 ± 5.69 |

Compared with the negative group, *p < 0.05, **p < 0.01; compared with the positive drug Opdivo group, Δp < 0.05, ΔΔ p < 0.01.

Experimental results showed that the proliferation of CD4+T and CD8+T cells in drug-resistant B16 melanoma and Lewis lung cancer mice was not obvious in positive drug OPDIVO® group and single drug chlorogenic acid group, but some proliferation was observed in the combination group of chlorogenic acid and coumaroylquinic acid, while in the test group of the combination of chlorogenic acid and coumaroylquinic acid+OPDIVO®, the increase in the number of D4+T and CD8+ T cells was extremely significant, indicating that the combination of chlorogenic acid and coumaroylquinic acid can effectively promote the proliferation of D4+T and CD8+ T cells in OPDIVO®-resistant B16 melanoma and Lewis lung cancer mice.

Example 5 Animal Experiment on the Treatment of Multidrug Resistance by Composition and Single Compound 1 Experimental Materials
1.1 Test Drugs
  Test drug 1: chlorogenic acid
  Test drug 2: coumaroylquinic acid
  Test drug 3: composition of chlorogenic acid and coumaroylquinic acid (100:0.01)
  Test drug 4: composition of chlorogenic acid and coumaroylquinic acid (100:0.05)
  Test drug 5: composition of chlorogenic acid and coumaroylquinic acid (100:0.1)
  Test drug 6: composition of chlorogenic acid and coumaroylquinic acid (100:0.5)
  Positive drug 1: dacarbazine (5-(3,3-dimethyl-1-triazenyl)-4-carboxamideimidazolium citrate).
  Positive drug 2: gemcitabine.
1.2 Test Cell Lines
  Lewis lung cancer cell lines were induced by the increased gradient concentration of dacarbazine and gemcitabine, and established by clone screening, then cultured without drug before the experiment.
1.3 Test Animals
  BABL/C-nu mice, ♀, weighing 18~22 g;
2 Experimental Method
2.1 Establishment of Tumor Model in Experimental Animals
  After the drug was removed from the drug-resistant cell lines, the cell concentration was adjusted to $1\times10^7$/ml with the culture medium. $1\times10^7$/ml of cells were subcutaneously injected into the right armpit of mice, 0.1 ml per mouse.
2.2 Administration Method
  After the average diameter of tumor reached 100 mm, the mice were randomly divided into test drug group 1, test drug group 2, test drug group 3, test drug group 4, test drug group 5, test drug group 6, positive drug group, and negative group, respectively.

Test drug group: the test drug group was first intraperitoneally injected, once a day, 30 mg/kg/time, for 5 consecutive days; administration was stopped, and the positive drug was given by intraperitoneal injection on the next day; wherein the positive drug dacarbazine was administrated once every other day, 60 mg/kg/time; wherein the positive drug gemcitabine was given once every other day, 300 mg/kg/time.

Positive drug group: positive drug dacarbazine was given once every other day, 60 mg/kg/time; positive drug gemcitabine was given once every other day, 300 mg/kg/time.

Negative group: normal saline was intraperitoneally injected, once a day, for 15 consecutive days.

2.3 Evaluation of Antitumor Effect

After completion of administration, the experiment was stopped, and the mice were killed by cervical dislocation and weighed. The tumor was stripped and weighed, to calculate the tumor inhibition rate.

Tumor inhibition rate %=[1−(the average tumor weight in the drug group/the average tumor weight in the negative group)]×100%.

2.4 Expression of PD-1/PD-L1

The positive expression rate of PD-1/PD-L1 in tumor tissues was detected by immunohistochemical SP method.

2.5 Determination of the Number of CD4+T and CD8+T Lymphocytes

The number of CD4+T and CD8+T lymphocytes was analyzed by immunofluorescence staining, and the average number of CD4+T and CD8+T cells infiltrated in 6 high power fields was counted.

3 Experimental Results 3.1 Effect of Each Experimental Group on the Inhibition Rate of Drug-Resistant Transplanted Tumor

TABLE 21

Effect of each experimental group on the weight and the inhibition rate of transplanted tumor in mice with multi-drug resistant Lewis lung cancer (x ± s).

| Groups | Dose (mg · kg$^{-1}$) | Aniaml number (n) | Tumor weight (g) | Tumor-inhibition rate (%) |
|---|---|---|---|---|
| Coumaroylquinic acid | 30 | 8 | 2.15 ± 0.72 | 8.90 |
| Chlorogenic acid | 30 | 8 | 1.92 ± 0.69 | 18.64 |
| Composition of chlorogenic acid and coumaroylquinic acid (100:0.01) + gemcitabine | 30 + 300 | 8 | 0.58 ± 0.31** ΔΔ | 75.42 |
| Composition of chlorogenic acid and coumaroylquinic acid (100:0.05) + gemcitabine | 30 + 300 | 8 | 0.51 ± 0.28** ΔΔ | 78.39 |
| Composition of chlorogenic acid and coumaroylquinic acid (100:0.1) + gemcitabine | 30 + 300 | 8 | 0.76 ± 0.47** ΔΔ | 67.80 |
| Composition of chlorogenic acid and coumaroylquinic acid (100:0.5) + gemcitabine | 30 + 300 | 8 | 0.92 ± 0.36** ΔΔ | 61.02 |
| Composition of chlorogenic acid and coumaroylquinic acid (100:0.01) + dacarbazine | 30 + 60 | 8 | 0.61 ± 0.44**## | 74.15 |
| Composition of chlorogenic acid and coumaroylquinic acid (100:0.05) + dacarbazine | 30 + 60 | 8 | 0.56 ± 0.15**## | 76.27 |
| Composition of chlorogenic acid and coumaroylquinic acid (100:0.1) + dacarbazine | 30 + 60 | 8 | 0.71 ± 0.22**## | 69.92 |
| Composition of chlorogenic acid and coumaroylquinic acid (100:0.5) + dacarbazine | 30 + 60 | 8 | 0.86 ± 0.18**## | 63.56 |
| Positive drug gemcitabine | 300 | 8 | 2.27 ± 0.38 | 3.81 |
| Positive drug dacarbazine | 60 | 8 | 2.33 ± 0.52 | 1.27 |
| Negative group | N.S | 8 | 2.36 ± 0.29 | — |

Compared with the negative group, *p < 0.05, **p < 0.01; compared with the positive drug gemcitabine group, Δp < 0.05, ΔΔ p < 0.01; compared with the positive drug dacarbazine group, #p < 0.05, ##p < 0.01.

Figure 7:
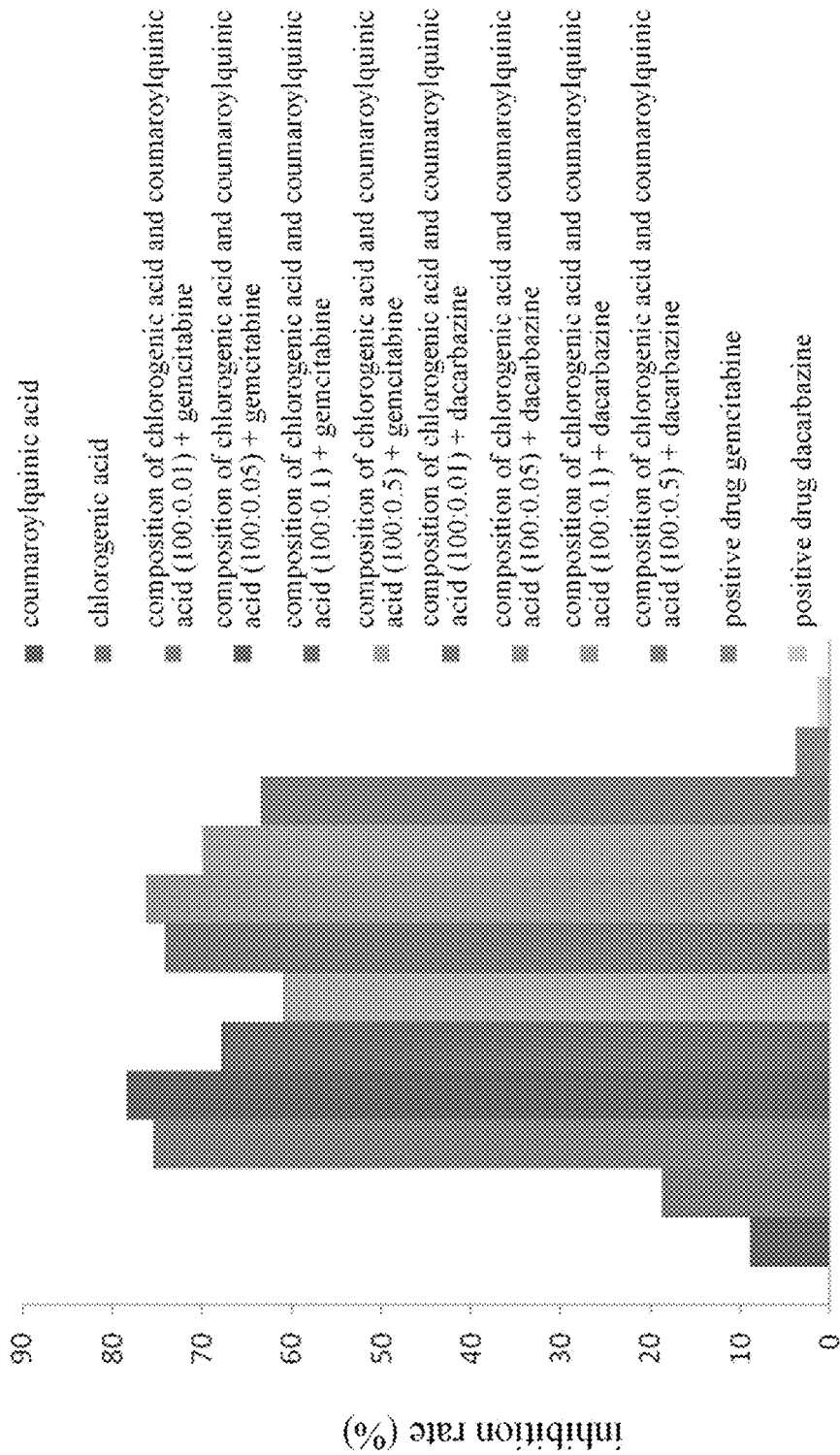
FIG. 7 shows the effect of each experimental group on the weight and the inhibition rate of transplanted tumor in mice with multidrug resistant Lewis lung cancer.

From Table 21 and FIG. 7, it can be shown that gemcitabine and dacarbazine in the positive drug groups have a lower inhibition rate on the transplanted tumor of mice with multidrug-resistant Lewis lung cancer, and both of groups don't have obvious inhibitory effect on the tumor. But in the test drug groups, coumaroylquinic acid, chlorogenic acid, and the combination of chlorogenic acid and coumaroylquinic acid have inhibitory effect on drug-resistant Lewis lung cancer, in which the tumor inhibitory rate of the combination of chlorogenic acid and coumaroylquinic acid is significant, indicating that the combination of chlorogenic acid and coumaroylquinic acid could effectively solve the multidrug resistance of Lewis lung cancer caused by gemcitabine and dacarbazine. In addition, according to the inhibition effect of single drug coumaroylquinic acid and chlorogenic acid in the test drug groups, the tumor inhibition rate is far lower than that of the combination of chlorogenic acid and coumaroylquinic acid, indicating that the combination of chlorogenic acid and coumaroylquinic acid can well reverse the multidrug resistance of Lewis lung cancer caused by gemcitabine and dacarbazine, and chlorogenic acid and coumaroylquinic acid have synergistic effect.

3.2 Expression of PD-1/PD-L1 in Drug-Resistant Transplanted Tumor of Each Experimental Group

TABLE 22

Expression rate of PD-1/PD-L1 in transplanted tumor tissues of B16 melanoma mice with multidrug resistance in each experimental group (%).

| Groups | Positive PD-L1 |
|---|---|
| Coumaroylquinic acid | 73.39% |
| Chlorogenic acid | 72.26% |
| Composition of chlorogenic acid and coumaroylquinic acid (100:0.01) + gemcitabine | 36.34% |
| Composition of chlorogenic acid and coumaroylquinic acid (100:0.05) + gemcitabine | 31.58% |
| Composition of chlorogenic acid and coumaroylquinic acid (100:0.1) + gemcitabine | 40.71% |
| Composition of chlorogenic acid and coumaroylquinic acid (100:0.5) + gemcitabine | 46.08% |
| Composition of chlorogenic acid and coumaroylquinic acid (100:0.01) + dacarbazine | 34.91% |
| Composition of chlorogenic acid and coumaroylquinic acid (100:0.05) + dacarbazine | 32.28% |
| Composition of chlorogenic acid and coumaroylquinic acid (100:0.1) + dacarbazine | 40.21% |
| Composition of chlorogenic acid and coumaroylquinic acid (100:0.5) + dacarbazine | 42.36% |
| Positive drug gemcitabine | 74.35% |
| Positive drug dacarbazine | 72.51% |
| Negative group | 76.24% |

Experimental results showed that the combination group of chlorogenic acid and coumaroylquinic acid could effectively inhibit the expression of PD-1/PD-L1 in the transplanted tumor tissues of B16 cancer mice with multidrug resistance, and both of chlorogenic acid and coumaroylquinic acid had synergistic effect, in which the combination of chlorogenic acid and coumaroylquinic acid in the ratio of 100:0.01~100:0.05 was the best.

3.3 the Number of CD4+T and CD8+T Cells in Multidrug-Resistant Transplanted Tumor of Each Experimental Group

TABLE 23

The number of CD4 + T and CD8 + T lymphocytes in the transplanted tumor of multidrug-resistant Lewis lung cancer mice in each experimental group (x ± s).

| Groups | CD4 + T cells | CD8 + T cells |
|---|---|---|
| Coumaroylquinic acid | 79.11 ± 5.36 | 122.08 ± 14.36 |
| Chlorogenic acid | 79.24 ± 4.06 | 126.52 ± 11.85 |
| Composition of chlorogenic acid and coumaroylquinic acid (100:0.01) + gemcitabine | 133.55 ± 13.41ΔΔ | 236.94 ± 9.56ΔΔ |
| Composition of chlorogenic acid and coumaroylquinic acid (100:0.05) + gemcitabine | 147.23 ± 8.36ΔΔ | 247.15.12 ± 11.21ΔΔ |
| Composition of chlorogenic acid and coumaroylquinic acid (100:0.1) + gemcitabine | 132.74 ± 10.25ΔΔ | 225.93 ± 8.52ΔΔ |
| Composition of chlorogenic acid and coumaroylquinic acid (100:0.5) + gemcitabine | 106.07 ± 11.85ΔΔ | 196.68 ± 15.25ΔΔ |
| Composition of chlorogenic acid and coumaroylquinic acid (100:0.01) + dacarbazine | 128.89 ± 8.36**## | 228.05 ± 12.63**## |
| Composition of chlorogenic acid and coumaroylquinic acid (100:0.05) + dacarbazine | 145.03 ± 12.33**## | 252.81 ± 14.41**## |
| Composition of chlorogenic acid and coumaroylquinic acid (100:0.1) + dacarbazine | 126.39 ± 9.09**## | 206.74 ± 8.73**## |
| Composition of chlorogenic acid and coumaroylquinic acid (100:0.5) + dacarbazine | 119.52 ± 12.52**## | 179.39 ± 13.08**## |
| Positive drug gemcitabine | 77.69 ± 8.96 | 121.08 ± 10.32 |
| Positive drug dacarbazine | 74.52 ± 7.38 | 123.74 ± 12.85 |
| Negative group | 73.42 ± 5.11 | 118.52 ± 14.36 |

Compared with the negative group, $*p < 0.05$, $**p < 0.01$; compared with the positive drug gemcitabine group, $\Delta p < 0.05$, $\Delta\Delta p < 0.01$; compared with the positive drug dacarbazine group, $\#p < 0.05$, $\#\#p < 0.01$.

Experimental results showed that the number of CD4+T and CD8+T cells in the experimental group of the combination of chlorogenic acid and coumaroylquinic acid was significantly higher than that in the positive drug groups (dacarbazine and gemcitabine), indicating that the combination of chlorogenic acid and coumaroylquinic acid can effectively promote the proliferation of CD4+T and CD8+T cells in multidrug-resistant Lewis lung cancer mice, and chlorogenic acid and coumaroylquinic acid have a synergistic effect.

In summary, the present invention provides a pharmaceutical composition, which comprises chlorogenic acid and coumaroylquinic acid, and the combination can be used to prepare reversal agents of tumor multidrug resistance and PD-1/PD-L1 inhibitors. The experimental results of the present invention show that the combined use of chlorogenic acid and coumaroylquinic acid can play a synergistic effect. In particular, the combined use of chlorogenic acid and coumaroylquinic acid has a good reversal effect on tumor cell lines with multi-drug resistance to chemotherapeutic drugs and immunotherapeutic drugs, and can effectively solve the drug resistance of B16 melanoma cell lines caused by dacarbazine and the drug resistance of Lewis lung cancer induced by gemcitabine, as well as can effectively inhibit the expression of PD-1/PD-L1 in the transplanted tumor tissues of B16 melanoma mice and Lewis lung cancer mice with drug resistance, and effectively reverse the drug resistance of B16 melanoma cell lines and Lewis lung cancer cell lines caused by OPDIVO®, and can effectively promote the proliferation of CD4+T and CD8+T cells in drug-resistant B16 melanoma mice and Lewis lung cancer mice.

The invention claimed is:

1. A method for treating multidrug resistance to a tumor, comprising administering to a subject in need thereof a reversal agent, wherein the reversal agent comprises chlorogenic acid and a coumaroylquinic acid at a mass ratio of chlorogenic acid to coumaroylquinic acid of 100:0.01 to 100:0.5, wherein said tumor is melanoma or lung cancer, and is resistant to dacarbazine, gemcitabine, or nivolumab.

2. The method according to claim 1, wherein the mass ratio of chlorogenic acid to coumaroylquinic acid is 100:0.01 to 100:0.1.

3. The method according to claim 1, wherein the mass ratio of chlorogenic acid to coumaroylquinic acid is 100:0.05.

4. The method according to claim 1, wherein the reversal agent further comprises a pharmaceutically acceptable excipient.

5. The method according to claim 1, wherein the reversal agent is an oral or injectable preparation.

6. A method for treating a tumor, comprising:
   administering to a subject in need thereof an antitumor drug and a reversal agent,
   wherein the antitumor drug is dacarbazine, gemcitabine, or nivolumab,
   wherein the reversal agent comprises chlorogenic acid and a coumaroylquinic acid at a mass ratio of chlorogenic acid to coumaroylquinic acid of 100:0.01 to 100:0.5, and
   wherein said tumor is melanoma or lung cancer.

7. The method according to claim 6, wherein the mass ratio of chlorogenic acid to coumaroylquinic acid is 100:0.01 to 100:0.1.

8. The method according to claim 7, wherein the mass ratio of chlorogenic acid to coumaroylquinic acid is 100:0.05.

9. The method according to claim 6, wherein the reversal agent further comprises a pharmaceutically acceptable excipient.

10. The method according to claim 6, wherein the reversal agent is an oral or injectable preparation.

11. The method according to claim 6, wherein the reversal agent and the antitumor drug are administered separately.

* * * * *